(12) United States Patent
Shelby et al.

(10) Patent No.: US 7,794,761 B2
(45) Date of Patent: Sep. 14, 2010

(54) METHODS FOR INDUCING ANTI-ANXIETY AND CALMING EFFECTS IN ANIMALS AND HUMANS

(75) Inventors: Nancy J. Shelby, Bozeman, MT (US); Mitchell T. Godfrey, Bozeman, MT (US); Mark J. Rosenfeld, Draper, UT (US)

(73) Assignee: Seroctin Research & Technology, Inc., Salt Lake City, UT (US)

( * ) Notice: Subject to any disclaimer, the term of this patent is extended or adjusted under 35 U.S.C. 154(b) by 1236 days.

(21) Appl. No.: 11/178,998

(22) Filed: Jul. 11, 2005

(65) Prior Publication Data

US 2005/0250772 A1    Nov. 10, 2005

Related U.S. Application Data

(63) Continuation-in-part of application No. 10/845,388, filed on May 13, 2004, and a continuation-in-part of application No. 10/718,232, filed on Nov. 20, 2003, now abandoned, which is a continuation-in-part of application No. 09/834,592, filed on Apr. 13, 2001, now Pat. No. 6,667,308.

(60) Provisional application No. 60/587,167, filed on Jul. 12, 2004, provisional application No. 60/196,829, filed on Apr. 13, 2000.

(51) Int. Cl.
 A61K 36/89 (2006.01)
 A61K 31/428 (2006.01)
 A61K 31/538 (2006.01)

(52) U.S. Cl. .................... 424/750; 514/230.5; 514/375; 514/376

(58) Field of Classification Search .................. None
See application file for complete search history.

(56) References Cited

U.S. PATENT DOCUMENTS

| | | | |
|---|---|---|---|
| 4,457,872 A | 7/1984 | Murase et al. | |
| 4,558,060 A | 12/1985 | Caignard et al. | |
| 4,778,792 A | 10/1988 | Lesieur et al. | |
| 4,960,778 A | 10/1990 | Lesieur et al. | |
| 5,071,863 A | 12/1991 | Ito et al. | |
| 5,147,883 A | 9/1992 | Aichaioui et al. | |
| 5,179,091 A | 1/1993 | Lesieur et al. | |
| 5,182,278 A | 1/1993 | Lesieur et al. | |
| 5,196,434 A | 3/1993 | Tavernet et al. | |
| 5,240,919 A | 8/1993 | Yous et al. | |
| 5,292,735 A | 3/1994 | Sugimoto et al. | |
| 5,296,477 A | 3/1994 | Taverne et al. | |
| 5,300,507 A | 4/1994 | Yous et al. | |
| 5,322,843 A | 6/1994 | Yous et al. | |
| 5,322,849 A | 6/1994 | Yous et al. | |
| 5,326,775 A | 7/1994 | Yous et al. | |
| 5,386,034 A | 1/1995 | Yous et al. | |
| 5,436,348 A | 7/1995 | Yous et al. | |
| 5,688,820 A | 11/1997 | Mouithys-Mickalad et al. | |
| 5,786,367 A | 7/1998 | Oshiro et al. | |
| 5,919,784 A | 7/1999 | Lesieur et al. | |
| 6,177,422 B1 | 1/2001 | Belliotti et al. | |
| RE37,478 E | 12/2001 | Strupczewski et al. | |
| 6,667,308 B2 | 12/2003 | Rosenfeld et al. | |
| 7,524,877 B2 * | 4/2009 | Rosenfeld et al. | 514/376 |
| 2004/0192669 A1 * | 9/2004 | Rosenfeld et al. | 514/211.06 |
| 2004/0209877 A1 * | 10/2004 | Shelby et al. | 514/230.5 |
| 2006/0148795 A1 * | 7/2006 | Rosenfeld et al. | 514/230.5 |
| 2006/0160795 A1 * | 7/2006 | Rosenfeld et al. | 514/230.5 |
| 2006/0166981 A1 * | 7/2006 | Rosenfeld et al. | 514/230.5 |
| 2006/0173001 A1 * | 8/2006 | Rosenfeld et al. | 514/230.5 |
| 2006/0223796 A1 * | 10/2006 | Rosenfeld et al. | 514/230.5 |

FOREIGN PATENT DOCUMENTS

| | | |
|---|---|---|
| CH | 683593 | 4/1994 |
| DE | 670 584 | 1/1939 |
| EP | 0070016 A1 | 1/1983 |
| EP | 0478446 | 4/1992 |
| EP | 0 506 539 | 9/1992 |
| EP | 0506539 | 9/1992 |

OTHER PUBLICATIONS

Loomis et al. Plant Physiology. 1957. vol. 32, No. 5, pp. 379-385.*
Tang et al. Phytochemistry. 1975. vol. 14, No. 9, pp. 2077-2079.*
Smissman et al. J. Org. Chem. 1957. vol. 22, p. 220.*
Virtanen et al. Arch. Biochem. Biophys. 1957. vol. 69, p. 486-500.*
Kluge et al. PHytochem. 1997. vol. 44, No. 4, pp. 639-641.*
Kato-Noguchi., H. Phytochem. 1999. vol. 52, pp. 1023-1027.*
Perez et al. Phytochem. 1985. vol. 24, No. 12, pp. 2963-2966.*
Zhang et al. J. Med. Chem. 1995. vol. 38, No. 4, pp. 735-738.*
Garcia H.L., "Dermatological complications,"PuBMed Abstr. 12180897; *American Journal of Clinical Dermatology*, 3(7): 497-506, 2002.
Lee, HS., "Tyrosinase inhibitors of Pulsatilla cernua root-derived materials," PubMed Abstr. 11879010, *Journal of Agricultural Food Chemicals*, 50(6): 140, 2002.
Pischon et al., "Recent developments in the treatment of obesity," PuBMed Abstr. 12187313, *Current Opinions of Nephrological Hypertension*, 11(5): 497-502, 2002.

(Continued)

*Primary Examiner*—Christopher R. Tate
(74) *Attorney, Agent, or Firm*—Workman Nydegger

(57) ABSTRACT

Phenolic compounds with a phenolic molecule to which are covalently linked an oxygen-containing group, a nitrogen or another oxygen containing group, and a $C_1$-$C_4$ alkoxy group, or their precursor compounds, obtainable from monocotyledonous plants, or by chemical synthesis, have been found to calm and/or reduce anxiety and related behaviors and states in humans and animals. Additional chemical compounds of the present invention may include benzoxazinoids-cyclic hydroxyamic acids, lactams, and corresponding glucosides, which may serve as precursors to phenolic compounds. The phenolic compounds and precursors of phenolic compounds of the present invention, at concentrations suitable for human and animal therapeutic use, may be obtained from monocotyledonous plants such as corn in their early growth states which are timely harvested for optimum yield.

24 Claims, 4 Drawing Sheets

OTHER PUBLICATIONS

Wang et al., "Hypotensive activity of the pineal indoleamine hormones melatonin, 5-methoxytryptophol and 5-méthoxytryptamine,"PubMed Abstr. 10752670, *Pharmacological Toxicology*, 86(3): 125-8, 2000.

Katz et al., "Central obesity, depression and the hypothalamo-pituitary-adrenal axis in men and postmenopausal women," *International Journal of Obesity Related Metabolism Disorders*, 24: 246-51, 2000.

McGahuey et al., "The Arizona Sexual Experience Scale (ASEX): reliability and validity," *Journal of Sex & Marital Therapy*, 26: 25-40, 2000.

Griffen et al., "Selective serotonin reuptake inhibitors directly alter activity of neurosteroidogenic enzymes," *Proceedings of Natural Academy Sciences* (Washington D.C.), 96(23): 13512-13517, 1999.

Rudolf et al., "Subjective quality of life in female in-patients with depression: A longitudinal study," *International Journal of Social Psychiatry*, 45(4): 238-46, 1999.

Negus et al., "Reproductive strategies of *Dicrostonyx groenlandicus* and *Lemmus sibiricus* in high-arctic tundra," *Canadian Journal of Zoology*, 76: 391-399, 1998.

Gianoli et al., "Characteristics of hydroxamic acid induction in wheat triggered by aphid infestation," *Journal of Chemical Ecology*, 23(12): 2695-2705, 1997.

Niemeyer et al., "Chromosomal location of genes for hydroxamic acid accumulation in *Triticum aestivum* L. (wheat) using wheat aneuploids and wheat substitution lines," *Heredity*, 79: 10-14, 1997.

Dowd et al., "Enzymatic oxidation products of allelochemicals as a basis for resistance against insects: effects on the corn leafhopper *Dalbulus maidis,*" *Natural Toxins*, 4:85-91, 1996.

Cooksey, C.; "A Simple One Pot Reaction of 4-Alkoxy and 4-Alkylthio-Catechols and O-Benzoquinones"; *Organic Preparations and Procedures Int.*, vol. 28, No. 4, 1996, 463-467.

Meek et al., "Interation of maternal photoperiod history and food type on growth and reproductive development of laboratory meadow voles (*Microtus pennsylvanicus*)," *Physiology and Behavior*, 57(5): 905-11, 1995.

Bergvinson et al., "Putative role of photodimerized phenolic acids in maize resistance to *Ostrinia nubilalis* (Lepidoptera: Pyralidae)," *Environmental Entomology*, 23(6): 1516-1523, 1994.

Hayashi et al., "6-Methoxy-2-benzoxazolinone in *Scoparia dulcis* and its production by cultured tissues," *Phytochemistry*, 37(6): 1611-1614, 1994.

Leighton et al., "Substrate specificity of a glucosyltransferase and an N-hyroxylase involved in the biosynthesis of chyclic hydroxamic acids in Gramineae," *Phytochemistry*, 36(4): 887-892, 1994.

Mayoral et al., "A high performance liquid chromatography method for quantification of DIBOA, DIMBOA, and MBOA from aqueous extracts of corn and winter cereal plants," *Journal of Liquid Chromatography*, vol. 17, No. 12, pp. 2651-2665, 1994.

Hoshi-Sakoda, M.; "Structure Activity Relationships of Enzoxazolinones with Respect to Auxin-Induced Growth and Auxin-Binding Protein"; *Phytochemistry*, vol. 37, No. 2, 1994, 297-300.

Assabgui et al., "Hydroxamic acid content of maize (*Zea mays*) roots of 18 Ontario hybrids and prediction of antibiosis to western corn rootworm, *Diabrotica virgfera virgifera* Leconte ( *Cleoptera: Chrysomelidae*)," *Canadian Journal of Plant Science*, 73: 359-363, 1993.

Cuevas et al., "Effect of hydroxamic acids from cereals on aphid cholinesterases," *Phytochemistry*, 34(4): 983-985, 1993.

Frandsen et al., "Maternal transfer of the 6-MBOA chemical signal in *Microtus montanus* during gestation and lactation," *Canadian Journal of Zoology*, 71: 1799-1803, 1993.

Richardson et al., "Cyclic hydroxamic acid accumulation in corn seedlings exposed to reduced water potentials before, during, and after germination," *Journal of Chemical Ecology*, 19(8): 1613-1624, 1993;* Assabgui et al., "Hydroxamic acid content of maize roots of 18 Ontario hybrids and prediction of antibiosis to western corn rootworm," *Canada Journal of Plant Science*, 73: 359-363, 1993.

Bjostad, Louis B. and Hibbard, Bruce E., "6—Methoxy-2-Benzoxazolinone: a Semiochemical for Host Location by Western Corn Rootworm Larvae," *Journal of Chemical Ecology*, vol. 18, No. 7, pp. 931-944, 1992.

Arnason et al., "Phototoxins in plant-insect interactions. In Herbivores, Their interactions with secondary plant metabolites," Edited by M. Berenbaum et al., Academic Press, N.Y.; *Ecological and evolutionary processes*, pp. 317-341 vol. II. $2^{nd}$ Ed., 1992.

Givovich et al., "Hydroxamic Acid Glucosides in Honeydew of Aphids Feeding on Wheat," Journal of chemical Ecology, vol. 18 No. 6:841-846, 1992.

Blum et al., "Allelopathic activity in wheat-conventional and wheat-no-till soils: development of soil extract bioassays," *Journal of Chemical Ecology*, 18(12): 2191-2221, 1992.

Nicol et al., "A screen of worldwide wheat cultivars for hydroxamic acid levels and aphid antixenosis," *Annotated Applied Biology*, 121: 11-18, 1992.

Copaja et al., "Hydroxamic acid content of perennial Triticeae," *Phytochemistry*, 30(5): 1531-1534, 1991a.

Copaja et al., "Hydroxamic acid levels in Chilean and British wheat seedlings," *Ann. Applied Biology*, 118: 223-227, 1991b.

Moffatt et al., "Effects of photoperiod and 6-methoxy-2 benzoxazolinone on male-induced estrus in prairie voles," *Physiology and Behavior*, 49: 27-31, 1991.

Xie et al., "Distribution and variation of hydroxamic acids and related compounds in maize (*Zea mays*) root system," *Canadian Journal of Botany*, 69: 677-681, 1991.

Zuniga et al., "Hydroxamic acid content in undifferentiated and differentiated tissues of wheat," *Phytochemistry*, 30(10): 3281-3283, 1991.

Perez et al., "Difference in hydroxamic acid content in roots and root exudates of wheat (*Triticum aestivum* L.) and rye (*Secale cereale* L.): possible role in allelopathy," *Journal of Chemical Ecology*, 17(6): 1037-1043, 1991.

Daya et al., "Effect of 6-methoxy-2-benzoxazolinone on the activities of rat pineal N-acetyltransferase and hydroxyindole-O-methyltransferase and on melatonin production," *Journal of Pineal Research*, 8: 57-66, 1990.

Gower, B.A., "Endocrine effects of the naturally occurring reproductive stimulant, 6-methoxybenzoxazoline," Ph.D. Thesis, University of Utah, Salt Lake City, Utah, 116 pp. 1990.

Gower et al., "Reproductive responses of male *Microtus montanus* to photoperiod, melatonin, and 6-MBOA," *Journal of Pineal Research*, 8: 297-317, 1990.

Nelson et al., "Photoperiod affects reproductive responsiveness to 6-methoxy-2-benzoxazolinone in house mice," *Biology of Reproduction*, 43: 586-91, 1990.

Reid et al., "Resistance of maize germ plasm to European corn borer; *Ostrinia nubilalis*, as related to geographical origin," *Canadian Journal of Botany*, 68: 311-316, 1990.

Urbanski et al., "Influence of photoperiod and 6-methoxybenzoxazolinone on the reproductive axis of inbred LSH/Ss Lak male hamster," *Journal of Reproduction and Fertility*, 90: 157-162, 1990.

Niemeyer et al., "Changes in hydroxamic acid levels of wheat plants induced by aphid feeding," *Phytochemistry*, 28(2): 447-449, 1989.

Rowsemitt et al., "Reproductive function in *Dipodomys ordii* stimulated by 6-methoxybenzoxazolinone," *Journal of Mammology*, 70(4): 805-809, 1989.

Butterstein et al., "The plant metabolite 6-methoxybenzoxazolinone interacts with follicle-stimulating hormone to enhance ovarian growth," *Biology of Reproduction*, 39: 465-71, 1988.

Campos et al., "Toxicity and toxicokinetics of 6-methoxybenzoxazolinone (MBOA) in the European corn borer *Ostrinia nubilalis* (Hubner)," *Journal of Chemical Ecology*, 14(3): 989-1002, 1988.

Schadler et al., "The plant metabolite, 6-methoxybenzoxazolinone, stimulates an increase in secretion of follicle-stimulating hormone and size of reproductive organs in *Microtus pinetorum,*" *Biology of Reproduction*, 38: 817-820, 1998.

Sweat et al., "Uterotropic 6-methoxybenzoxazolinone is an adrenergic agonist and melatonin analog," *Molelcular Cellular Endocrinology*, 57: 131-138, 1988.

Anderson et al., "Effects of melatonin and 6-methoxybenzoxazolinone on photoperiodic control of testis size in adult male golden hamsters," *Journal of Pineal Research*, 5: 351-65, 1988.

Vaughan et al., "Hormonal consequences of subcutaneous 6-methoxy-2-benzoxazolinone pellets or injections in prepubertal male and female rats," *Journal of Reproduction and Fertility*, 83: 859-66, 1988.

Barnes et al., "Role of benzoxazinones in allelopathy by rye (*Secale cereale* L.)," *Journal of Chemical Ecology*, 13(4): 889-906, 1987.

Brice, C., "The effect of 6-methoxybenzoxazolinone on laboratory mice," Ph.D. Thesis, University of London, London, England, 1987.

Korn et al., "Initiation of breeding in a population of *Microtus townsendii* (Rodentia) with the secondary plant compound 6-MBOA," *Oecologia* (Berl.), 71: 593-596, 1987.

Barnes et al., "Isolation and characterization of allelochemicals in rye herbage," *Phytochemistry*, 26(5): 1385-1390, 1987.

Berger et al., "Effect of 6-methoxybenzoxazolinone on sex ratio and breeding performance in *Microtus montanus*," *Biology of Reproduction*, 1987; 36: 255-260, 1987.

Alibhai, S.K., "Reproductive response of *Gerbillus harwoodii* to 6-MBOA in the Kora National Reserve, Kenya," *Journal of Tropical Ecology*, 2: 377-379, 1986.

Epstein et al., "Dynamics of 6-methoxybenzoxazolinone in winter wheat, Effects of photoperiod and temperature," *Journal of Chemical Ecology*, 12(10): 2011-2020, 1986.

Rosenblatt, D.H.; "An Anomalous Result of an Attempted Dakin Reaction"; *Journal of American Chemical Society*, vol. 75, 4607-4608.

Berger, et al., Effect of 6-Methoxybenzoxazolinone on Sex Ratio and Breeding Performance in *Microtus Montanus*, Biol. Repod, 36(2):255-60 (1987).

Epstein, et al. Dynamics of 6-Methoxybenzoxazolinone in Winter Wheat, J. of Chem. Ecol, vol. 12, No. 10 (1986).

Seroctin Research & Technologies, Inc. v. Unigen Pharmaceuticals, Inc. et al. In the United States District Court, For the District of Utah, Central Division, Case No. 2:07CV582, pleading entitled "Defendants' Preliminary Invalidity Contentions".

* cited by examiner

METHODS FOR INDUCING ANTI-ANXIETY AND CALMING EFFECTS IN ANIMALS AND HUMANS

RELATED APPLICATIONS

This application claims the benefit of U.S. Patent Application Ser. No. 60/587,167, filed Jul. 12, 2004, and entitled "METHODS FOR INDUCING ANTI-ANXIETY AND CALMING EFFECTS IN ANIMALS AND HUMANS," and is a continuation-in-part of U.S. patent application Ser. No. 10/845,388, filed May 13, 2004, and entitled "METHODS FOR AUGMENTING IMMUNE DEFENSES CONTEMPLATING THE ADMINISTRATION OF PHENOLIC AND INDOLEAMINE-LIKE COMPOUNDS FOR USE IN ANIMALS AND HUMANS" and U.S. patent application Ser. No. 10/718,232, filed Nov. 20, 2003, now abandoned and entitled "NOVEL COMPOUNDS FOR USE IN WEIGHT LOSS AND APPETITE SUPPRESSION IN HUMANS," which claim the benefit of U.S. patent application Ser. No. 09/834,592, filed Apr. 13, 2001, and entitled "NOVEL COMPOUNDS FOR USE AS ANTIDEPRESSANTS, APHRODISIACS, AND ADJUNCTIVE THERAPIES IN HUMANS," now issued as U.S. Pat. No. 6,667,308, which claims the benefit of U.S. provisional application Ser. No. 60/196,829, filed Apr. 13, 2000, and entitled "ANTIDEPRESSANT, APHRODISIAC, WEIGHT-LOSS AIDE, THERAPY FOR QUITTING NICOTINE OR ADDICTIVE DRUGS AND TREATMENT OF BETTERING REPRODUCTION IN HUMANS," all of which are hereby incorporated herein by reference.

BACKGROUND

1. Field of the Invention

This invention relates to compositions for calming and reducing anxiety in humans and animals and, more particularly, to novel compositions of phenolic and indoleamine-like compounds obtainable in concentrations and amounts suitable for animal and human use derived, isolated, and/or extracted from certain botanicals or from chemical synthesis, together with methods for using, producing, and harvesting the same for use in calming and/or reducing anxiety in humans and animals suffering from anxiety disorders and related behaviors or during periods of stress, illness, or injury.

2. The Background Art

An estimated 35-40 million living Americans will suffer major depressive episodes, and many more will experience lesser bouts. Of the approximately 17.5 million Americans with ongoing depressions, about 9.2 million are at a clinically debilitating level. Clinical depression is characterized by a list of symptoms that last over a long time span. As appreciated by those skilled in the art, depression is a serious problem that is generally initiated or caused by outside stressors. As stresses escalate or persist, a chemical imbalance of the body usually results.

Clinical depression can be very debilitating both physically and mentally and even lead to death by means of suicide. Lost productivity and relationship problems may be consequences of lesser depressions. Presently, antidepressant medications are the cornerstones of treating depression, especially those that are at least moderately severe. Although depressed individuals and animals tend to improve when treated with antidepressants, many do not respond to the first antidepressant prescribed. Such individuals or animals may eventually benefit from a different antidepressant or, if sufficiently efficacious, a combination of suitable antidepressants.

Sexual dysfunction is another pervasive disorder. In the overall population, it is believed that forty-three percent (43%) of women and thirty-one percent (31%) of men between the ages of 18 and 59 experience sexual dysfunction and some repeatedly. As will be appreciated, sexual dysfunction may include, for example, a lack of interest in sex, problems with arousal, not enjoying sex, and anxiety associated with sexual performance. Indeed, feeling good in general has been found to have a significant impact on sexual function. In this regard, those people who are unhappy or depressed may be more likely to experience difficulties associated with sexual dysfunction. Arousal problems affect over 20 million American males (i.e., about 2 in 10 adult men), with such difficulties often associated with or accompanied by some sort of depression or mood disorder. Meanwhile, prescription antidepressants have been found to actually exacerbate the situation, since a frequent side effect of their use is sexual dysfunction. In fact, sexual response may actually diminish in up to seventy-five percent (75%) of prescription antidepressant users for using the same. To this end, there is a need for forms of treatment that reduce depression or otherwise better mood with an accompanying enhancement of sexual response, arousal or desire or, in the alternative, do not have a negative impact on a person's or animal's sexual function.

Prior work by those skilled in the art in connection with the compounds of the present invention have been primarily focused on 6-methoxy-2,3-benzoxazolinone (6-MBOA). For example, the role of 6-MBOA in strengthening the resistance of monocotyledonous plants against a wide range of insect pests has been much studied. It has been further proven that 6-MBOA and its chemical precursors may also have allelopathic properties that may inhibit root and shoot growth in competing species. Moreover, it has been found that 6-MBOA may have antimicrobial properties, wherein 6-MBOA appears constitutively during early stages of growth, localized in those tissues most exposed to microbial and insect attack.

It had been long suspected that compounds in plants affect the seasonal reproductive output of wild rodents. In 1981, 6-MBOA became the first naturally occurring compound in a plant that was verified as impacting seasonal reproductive cycling. As readily known, 6-MBOA may be found in varying concentrations in monocotyledonous plants. Since then, a substantial body of work has accumulated on 6-MBOA as an initiator of seasonal breeding and an effector of population size for many rodents and a few birds. Compounds related to and possibly co-occurring with 6-MBOA remain generally unexplored in this regard.

6-MBOA may be passed from adult females to offspring during gestation and lactation, which typically results in increased growth and larger gonads in the recipient young. Juveniles rely on the interaction of maternal photoperiod history and 6-MBOA to time the onset of growth and puberty. It has been found that adult animals that are fed a diet containing 6-MBOA produce more female progeny. Similarly, when 6-MBOA is fed to pregnant females, gonadal development in the male offspring is usually enhanced.

In rodents, it has been found that the inhibitory effects of melatonin on growth and reproduction are blocked partially by 6-MBOA (Gower et al., "Reproductive responses of male Microtus montanus to photo period, melatonin, and 6-MBOA", *Journal of Pineal Research*, 8: 297-312, 1990). As further shown by those skilled in the art, 6-MBOA may obstruct melatonin at the melatonin receptors or act independently to check melatonin action (Sweat et al., "Uterotropic 6-methoxybenzoxazolinone is an adrenergic agonist and melatonin analog," *Molecular and Cellular Endocrinology,* 57:131-138, 1988).

The high melatonin levels induced by 6-MBOA may also cause desensitization of melatonin receptors (Daya et al., "Effect of 6-methoxy-2-benzoxazolinone on the activities of rat pineal N-acetyltransferase and hydroxyindole-O-methyltransferase and on melatonin production," *Journal of Pineal Research,* 8:57-66, 1990), but not for all rodents (Anderson et al., "Effects of melatonin and 6-methoxybenzoxazolinone on photoperiodic control of testis size in adult male golden hamsters," *Journal of Pineal Research,* 5:351-65, 1988).

Further findings of those skilled in the art suggest that 6-MBOA stimulates rather than inhibits melatonin biosynthesis and does not prevent stimulation of melatonin synthesis by norepinephrine (Yuwiler et al., "Effects of 6-methoxy-2-benzoxazolinone on the pineal melatonin generating system," *J. Pharmacol. Exp. Ther.* 233:45-50, 1985). Moreover, 6-MBOA may act at both the alpha-($\alpha$) and beta-($\beta$) adrenergic receptors (Daya et al., "Effect of 6-methoxy-2-benzoxazolinone on the activities of rat pineal N-acetyltransferase and hydroxyindole-O-methyltransferase and on melatonin production," *Journal of Pineal Research,* 8:57-66, 1990), and may stimulate adenylcyclase (i.e., adenylate cyclase) activity in the pineal, hypothalamus and pituitary glands (Sweat et al., "Uterotropic 6-methoxy-benzoxazolinone is an adrenergic agonist and melatonin analog," *Molecular and Cellular Endocrinology,* 57:131-138, 1988).

As appreciated, certain responses to 6-MBOA, like uterine hypertrophy, can be duplicated with estrogen, but 6-MBOA is not an estrogenic compound (Gower, "Endocrine effects of the naturally occurring reproductive stimulant, 6-methoxybenzoxazolinone," Ph.D. Thesis, University of Utah, Salt Lake City, Utah, 1990). Also, 6-MBOA may increase the rate of synthesis of follicle stimulating hormone (Butterstein et al., "The plant metabolite 6-methoxybenzoxazolinone interacts with follicle-stimulating hormone to enhance ovarian growth," *Biology of Reproduction,* 39:465-71, 1988) and pituitary prolactin (Vaughan et al., "Hormonal consequences of subcutaneous 6-methoxy-2-benzoxazolinone pellets or injections in prepubertal male and female rats," *Journal of Reproduction and Fertility,* 83:859-66, 1988). In addition, hypothalamic luteinizing hormone-releasing hormone contents and pituitary gland weights are greater for at least one rodent species implanted with capsules containing 6-MBOA (Urbanski et al., "Influence of photoperiod and 6-methoxybenzoxazolinone on the reproductive axis of inbred LSH/Ss Lak male hamsters." *Journal of Reproduction and Fertility,* 90:157-163, 1990).

The inventors of the present invention recognized that 6-MBOA and the indoleamine, melatonin, share a structural similarity. However, melatonin exacerbates symptoms of dysphoria in depressed people. 6-MBOA, as a melatonin agonist, could prove contrary in this regard and actually improve mood. Yet, the inventors are not aware of any prior art that has explored or suggested the use of 6-MBOA or related compounds as having psychotropic effects in humans, particularly with respect to depression or bettering mood. An object of the present invention is to develop therapies for depression and sexual dysfunction entailing use of compounds belonging to related chemical families, of which 6-MBOA is a member. Pursuant to this end, a further object is to develop methods for extracting, deriving, and/or isolating said compounds from plant and animal sources in amounts suitable for human therapeutic use.

In addition to the effects of stress on depression and mood disorders, as well as sexual performance (i.e., desire, arousal and performance), as outlined hereinabove, those skilled in the art may also appreciate the multiple effects of stress on the immune systems and anxiety levels in animals and humans. For example, animals may be at risk for immune dysfunction related to stress which may manifest as increased infections, morbidity, and mortality associated with shipping stress, surgery, weaning, performance or training, crowding, and/or mixing with unfamiliar animals. The costs of such immune impairment to the livestock and other food animal industries may be significant and is estimated at over $1 billion per year in the United States alone.

Stress in animals and humans may be due to physical, chemical or electromagnetic challenge; illness; injury; and/or psychologic factors. Typically, these factors induce physiological adaption within the body of the stressed animal or human. Adaption may manifest in a plurality of responses. Stress-induced changes in hormone production may include higher levels of corticosterone, an immunosuppressive hormone. Stress and anxiety induced neuroendocrine responses may be associated with changes in immune system function including alterations in levels of pro-inflammatory cytokines. These stress-induced responses may, accordingly, result in an increased susceptibility to viral and bacterial infection, and a greater possibility of complications associated with cytokine abnormalities and inflammatory processes.

Humans may demonstrate immune abnormalities that may increase the risk for infection and autoimmune reactions following a variety of stressful stimuli, including injury, surgery, infection, psychological stress, mental illness (e.g., depression), and physical challenges such as intense elite athlete training. The resulting complications due to immune impairment in humans may facilitate significant increased costs of medical care and lost work days.

Those skilled in the art, including ethnobotanists, pharmacognosists, medicinal chemists, and certain mental health care practitioners are constantly in search of new compounds derived or isolated from plant materials that have anti-anxiety properties. For example, anti-anxiety activity has been widely associated with kava kava and commercial products containing kava kava and claiming and anti-anxiety effects are widely known.

An object of the present invention is to develop compositions and methods for calming and reducing anxiety in animals and humans entailing use of compounds belonging to related chemical families, of which 6-MBOA is a member. Pursuant to this end, a further object is to develop methods for extracting, deriving, and/or isolating said compounds from plant and animal sources in amounts suitable for human therapeutic use.

While past research by those skilled in the art has attempted to isolate, identify, and characterize new plant compounds with anti-anxiety properties, 6-MBOA has heretofore previously not been identified or evaluated for calming and anti-anxiety properties. Therefore, novel compounds derived, isolated, extracted, produced, and/or harvested from monocotyledonous plants or by chemical synthesis and methods for using the same to reduce anxiety and related pathology in animals and humans would be a significant advancement in the art. Such novel compositions and methods are disclosed and taught herein.

BRIEF SUMMARY AND OBJECTS OF THE INVENTION

A primary object of the present invention is to provide novel chemical compositions derived, isolated, and/or extracted from monocotyledonous plants or by chemical synthesis, and methods for using said compositions to aid in calming humans and animals experiencing anxiety during periods of stress or due to anxiety conditions.

It is also an object of the present invention to provide novel chemical compositions derived, isolated, and/or extracted from monocotyledonous plants or by chemical synthesis, and methods for using said compositions to elevate levels of indolamines, for example, serotonin and melatonin in humans and animals.

It is a further object of the present invention to provide novel chemical compositions derived, isolated, and/or extracted from monocotyledonous plants or by chemical synthesis, which function as serotonin and/or melatonin analogs and/or agonists in mammals.

It is a still further object of the present invention to provide novel methods for growing monocotyledonous plants which results in an increased yield of 6-MBOA or other phenolic and indoleamine compounds.

In addition, it is an object of the present invention to provide novel methods for harvesting monocotyledonous plants which are efficient for producing 6-MBOA or other phenolic and indoleamine compounds.

Moreover, it is an object of the present invention to provide novel chemical compositions derived, isolated, and/or extracted from monocotyledonous plants or by chemical synthesis, and methods for using said compositions for suppressing the anxiety eliciting effects of the hypothalamic-pituitary-adrenal (HPA) axis.

It is also an object of the present invention to provide novel chemical compositions derived, isolated, and/or extracted from monocotyledonous plants or by chemical synthesis, and methods for using said compositions for counteracting detrimental behaviors associated with anxiety.

Additionally, it is an object of the present invention to provide novel chemical compositions derived, isolated, and/or extracted from monocotyledonous plants or by chemical synthesis, and methods for using said compositions to reduce levels of catecholamine compounds (e.g., epinephrine and norepinephrine) that may be increased due to anxiety.

It is a still further object of the present invention to provide novel chemical compositions derived, isolated, and/or extracted from monocotyledonous plants or by chemical synthesis, and methods for using said compositions to affect gamma-aminobutyric acid (GABA) levels in a fashion associated with the reduction or elimination of anxiety.

It is a still further object of the present invention to provide novel chemical compositions derived, isolated, and/or extracted from monocotyledonous plants or by chemical synthesis, and methods for using said compositions to affect the function of gamma-aminobutyric acid (GABA) receptors (e.g., allosteric modification of the receptor to increase duration and/or frequency of ion channel opening).

It is a still further object of the present invention to provide novel chemical compositions derived, isolated, and/or extracted from monocotyledonous plants or by chemical synthesis, and methods for using said compositions to decrease comorbid symptoms related to anxiety.

It is a still further object of the present invention to provide novel methods for growing and harvesting monocotyledonous plants to obtain phenolic compounds with a phenolic molecule to which are covalently linked an oxygen-containing group, a nitrogen or second oxygen containing group, and at least one $C_1$-$C_4$ alkoxy group.

Additionally, it is an object of the present invention to provide novel methods for preserving and augmenting innate immune defenses in humans and animals by administering phenolic compounds with a phenolic molecule to which are covalently linked an oxygen-containing group, a nitrogen or second oxygen containing group, and at least one $C_1$-$C_4$ alkoxy group.

It is another object of the present invention to provide novel methods for calming and/or reducing anxiety in humans and animals by administering phenolic compounds with a phenolic molecule to which are covalently linked an oxygen-containing group, a nitrogen or second oxygen containing group, and at least one $C_1$-$C_4$ alkoxy group.

It is also an object of the present invention to provide novel methods for growing and harvesting monocotyledonous plants to obtain precursors of phenolic compounds comprising benzoxazinoids-cyclic hydroxamic acid, lactams, and their corresponding glucosides.

Additionally, it is an object of the present invention to provide novel methods for preserving and augmenting innate immune defenses in humans and animals by administering precursors of phenolic compounds comprising benzoxazinoids-cyclic hydroxamic acid, lactams, and their corresponding glucosides.

Consistent with the foregoing objects, and in accordance with the invention as embodied and broadly described herein, it has been found that certain phenolic compounds and precursors of phenolic compounds, related to each other by shared structural similarities and having structural similarities with serotonin and/or melatonin, are effective for reducing symptoms of anxiety in humans and animals. As appreciated, the novel compounds of the present invention may naturally exist as plant secondary metabolites in the earlier growth of monocotyledonous plants, become concentrated from their ingestion within certain animal parts, or may be synthesized by chemical means. The present invention contemplates the therapeutic use of novel compounds derived, isolated, and/or extracted from monocotyledonous plants or by chemical synthesis for use in the reduction of anxiety in humans and animals.

One presently preferred embodiment of a therapeutic method of the present invention comprises the ingestion by human or animal of the novel compounds of the present invention over a certain period of time, or other means for getting the compounds of the present invention into the body. Both males and females benefit from ingesting the compounds of the invention, while still contained in dried leaves from monocotyledonous plants with such compounds or taken as purified and/or synthesized preparations. It appears, based on the findings of the inventors that the novel compounds of the present invention act as indoleamine analogs and/or agonists and assist in reducing anxiety related to stress.

As discussed in greater detail hereinbelow, one presently preferred embodiment of the present invention comprises the administration of phenolic compounds belonging to related chemical families of which 6-methoxy-2,3-benzoxazolinone (6-MBOA) is a member. These phenolic compounds share a structural similarity with melatonin and indoleamine compounds. Based on structural similarities with melatonin, compounds of the present invention were studied for their effects on symptoms related to anxiety. In one presently preferred embodiment of a method of the present invention, particular emphasis is placed on calming and reducing anxiety and related behaviors in humans and animals by the administration of a therapeutically effective amount of a composition of 6-MBOA or pharmaceutically acceptable salts thereof.

A source of the compounds of the present invention for use in reducing anxiety in humans and animals may be found in certain monocotyledonous plants in their early growth stages. To obtain the compounds of the present invention at concentrations suitable for human therapeutic use from these such monocotyledonous plants, the harvesting of these plants at an early life history stage and drying using explicit parameters, as well as specific analytical criteria to ascertain suitability, are employed. However, it is also possible to get the compounds of the present invention at concentrations suitable for human therapeutic use from animal parts, including, but not necessarily limited to, the velvet antler tips of deer and elk (Cervidae), where they become concentrated after ingestion by the animal of sprouting and otherwise immature grasses. Furthermore, the compounds of the present invention may also be obtained through chemical synthesis.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTIONS OF THE PREFERRED EMBODIMENTS

Figure 1:
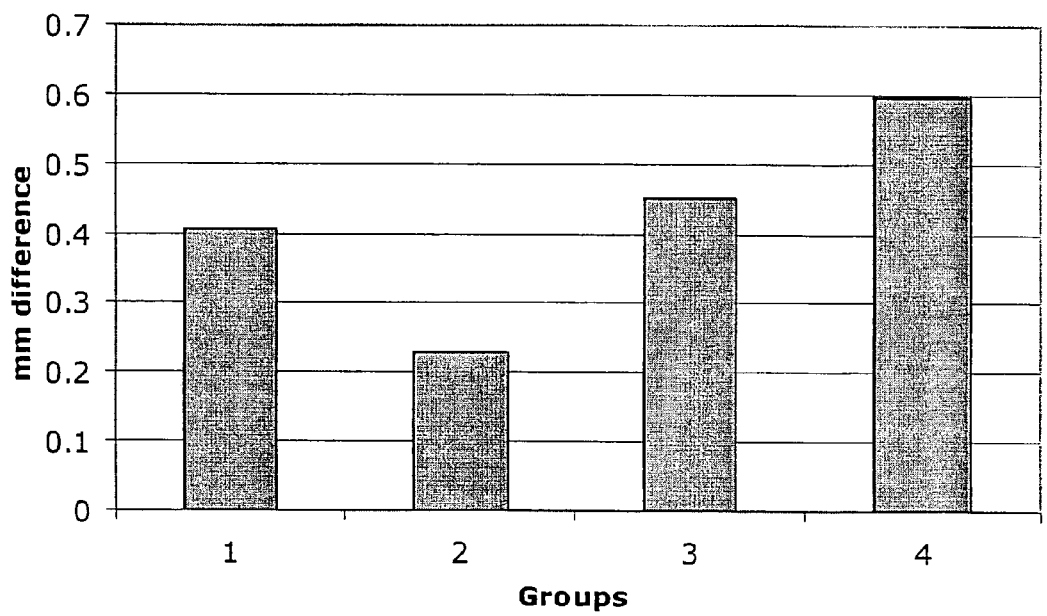
FIG. 1 is a bar chart illustrating a cellular immune response to dinitrofluoro-benzene (DNFB) resulting from a study examining ear swelling in stressed and non-stressed mice exposed to one presently preferred embodiment of compounds of the present invention and the corresponding stressed and non-stressed control mice.

It will be readily understood that the components of the present invention, as generally described and illustrated in the Figures, formulae and tables herein, could be arranged and designed in a wide variety of different configurations. Those of ordinary skill in the art will, of course, appreciate that various modifications to the details herein may be made without departing from the essential characteristics of the invention, as described. Thus, the following more detailed description of the embodiments of the compositions and methods of the present invention, as represented in FIGS. 1 through 4, is not intended to limit the scope of the invention, as claimed, but it is merely representative of the presently preferred embodiments of the invention.

Referring to Formulae I-IV below, the compounds of the invention have in common a phenol molecule to which are covalently linked an oxygen-containing group, a nitrogen- or another oxygen-containing group, and a $C_1$-$C_4$ alkoxy group. Using standard conventions for depicting chemical structures, Formulas I-III disclose the chemical structures and specific parameters defining the compounds of the invention. Formula IV is a unifying formula that depicts all the presently preferred embodiments of the compositions of the present invention.

Formula I—A chemical composition according to the formula

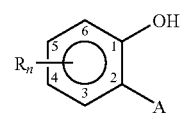

Wherein "R" represents $C_1$-$C_4$ alkoxy, with the proviso that R is in the 4 or 5 ring position;
Wherein "n" represents one of the integers 0, 1 or 2;
Wherein "A" represents —OH, —$NH_2$, or NHCR', where R' represents $C_1$-$C_4$ alkyl;
or pharmaceutically acceptable salts thereof.

Formula II—A chemical composition according to the formula

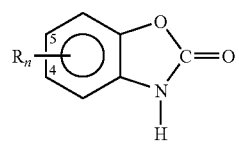

Wherein "R" represents $C_1$-$C_4$ alkoxy, with the proviso that R is in the 5 or 6 ring position;
Wherein "n" represents one of the integers 0, 1 or 2;
or pharmaceutically acceptable salts thereof.

Formula III—A chemical composition according to the formula

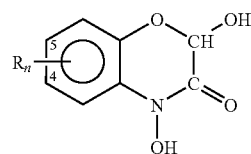

Wherein "R" represents $C_1$-$C_4$ alkoxy, with the proviso that R is in the 6 or 7 ring position;
Wherein "n" represents one of the integers 0, 1 or 2;
or pharmaceutically acceptable salts thereof.

Formula IV—A chemical composition according to the formula

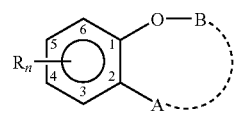

Wherein, "R" represents $C_1$-$C_4$ alkoxy, with the proviso that R is in the 4 or 5 ring position;

Wherein "n" represents one of the integers 0, 1 or 2;
Wherein "B" represents H and "A" represents —OH, —NH$_2$, or NHCR', where R' denotes C$_1$-C$_4$ alkyl; and "B A" represents

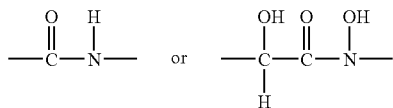

or pharmaceutically acceptable salts thereof.

It has been found that compounds of the invention, when ingested or otherwise introduced into the body of a human or animal, are effective as: (1) an antidepressant in that it betters mood and reduces or relieves symptoms of depression; (2) in sex therapies in the sense that it improves sexual desire and performance (e.g., desire, arousal, and performance); (3) an effective adjunctive therapy for weight loss; (4) as an adjunctive treatment for substance abuse and addiction; (5) for preserving and augmenting innate immune defenses in humans and animals; and (6) for reducing symptoms and comorbid behaviors relating to anxiety. The compounds may be administered in the form of ground parts of plants in which they naturally occur such as, by way of example but not by limitation, the ground leaves of immature corn, or as purified or chemically synthesized compounds in a pharmaceutically acceptable carrier.

The compounds of the present invention may be administered orally in the form of tablets, capsules, suspensions, solutions, or other means suitable for such ingestion, perhaps as an admixture with other compounds to enhance absorption into the blood stream or to otherwise assist in achieving the desired effects. Likewise, oral administration is contemplated to include sublingual (i.e., under the tongue) dosage forms. The compounds of the present invention may also be delivered by intranasal (i.e., through the nasal structures) or transmucosal (i.e., across mucous membranes) administration.

In addition, the compounds of the present invention may also be administered parenterally, as a subcutaneous, intramuscular, or intravenous injection, or by way of an implant for sustained release. When administered parenterally, the compounds of the present invention are to be dissolved in physiologically acceptable liquid media and/or otherwise compounded in accordance with the known pharmaceutical art. Another mode of administering the compounds of the present invention may be a transdermal patch, in which entry of the compounds of the invention into the body is facilitated via acceptable and appropriate carrier molecules.

Unless otherwise defined, the technical, scientific, and medical terminology used herein has the same meaning as understood by those informed of the art to which this invention belongs. However, for the purposes of establishing support for various terms that are used in the present application, the following technical comments, definitions, and review are provided for reference.

"Stress" may be defined as the failure of an animal or human to adapt to a stimulus or factor (e.g., physical, chemical, or emotional (as trauma, histamine, or fear, respectively)) and which causes physiologic tension that may predispose the animal or human to development of a disease or otherwise impair normal physiological function.

"Cytokines" may be defined as a class of immunoregulatory proteins (e.g., as interleukin, tumor necrosis factor, or interferon) that are secreted by cells. Cytokines are primarily secreted by cells associated with the immune system.

"Hormone" may be defined as a chemical product (often an organic chemical) of living cells that is secreted into body fluids where it may be transported to other areas of the body and produce a specific effect on the activity of cells.

"Immune system" may be defined as the system responsible for protecting the body of an animal or human from foreign substances, cells, and tissues. The immune system may include the thymus, spleen, lymph nodes, special deposits of lymphoid tissue (e.g., as in the gastrointestinal tract and bone marrow), antibodies, and lymphocytes (e.g., B cells and T cells).

"T-cell" may be defined as any of several lymphocytes that may undergo differentiation in the thymus. T-cells may possess highly specific cell-surface antigen receptors, and may be involved in controlling the initiation or suppression of cell-mediated and humoral immunity. T-cells may also possess receptors that lyse antigen-bearing cells.

"Cell mediated immunity (CMI)" may be defined as relating to the immune response mediated primarily by T-cells and especially cytotoxic T-cells rather than by antibodies secreted by B-cells.

"Catecholamines" may be defined as any of various chemical compounds (e.g., epinephrine, norepinephrine, dopamine, and the like) that may contain a benzene ring with two adjacent hydroxyl groups and a side chain of ethylamine. Catecholamine may function as hormones or neurotransmitters or, alternatively, may function as both.

"Corticoid" may be defined as any of various organic chemical compounds which may be extracted from the adrenal cortex. Corticoid may commonly refer to steroids or corticosteroids, several of which are hormones (e.g., corticosterone, cortisone, and aldosterone).

"Glucocorticoid" may refer to a corticoid that has a primary effect on carbohydrate metabolism (e.g., cortisone, hydrocortisone, prednisone, prednisolone, triamcinolone, methylprednisolone, dexamethasone, betamethasone, and the like).

"Innate" may be defined as existing in or belonging to a person, animal, or other living organism from birth. Innate may be used synonymously with native or natural.

"Immunity" may refer to the ability to resist a particular disease, especially by preventing the development of a pathogenic microorganism or by counteracting the effects of pathogenic microorganism toxins and cellular products.

"Natural immunity" may refer to immunity possessed by a group (i.e., a race, strain or species) and occurring in an individual as part of its genetic and/or biological makeup.

"Macrophage" may be defined as a large phagocyte. Wherein a phagocyte, typically a leucocyte or reticuloendothelial cell, may be any cell that characteristically engulfs foreign material. Phagocytes may function in the body to remove and consume debris and foreign bodies (e.g., degenerating tissue or bacteria).

"Complement" may refer to any thermolabile (i.e., inactivated by excessive heat) substances normally found in blood serum and plasma. Complement may work in combination with antibodies to cause the destruction of bacteria, foreign blood corpuscles, and other antigens.

"Antibody" may refer to any of various body globulin proteins which may be produced by cells of the specific immune system in response to infection or administration of suitable antigens or haptens (i.e., non-antigenic or weakly antigenic substance) and combine with the antigens (e.g., bacteria, toxins, or foreign red blood cells) to neutralize them and/or neutralize their toxins.

Many animals and all humans have an immune system for providing cellular and/or physiological defense mechanisms against foreign particles, for example and not by way of limitation, invading microbes and microorganisms (e.g., bacteria, viruses, amoeba, parasites, and the like), foreign proteins and carbohydrates, and other antigenic (i.e., stimulation of antibody and/or complement response) substances. The term "immunity" is often used interchangeably with immune system and its role in the body.

The term "inflammation" may generally refer to the process of the immune system in identifying a foreign particle, antigen, or damaged tissue, mobilizing cells, and molecules to attack the foreign particle, antigen or damaged tissue and disabling and/or destroying the foreign particle or antigen or eliminating damaged tissue. Inflammation often may be characterized by capillary dilatation, infiltration with leukocytes (i.e., white blood cells), localized and/or generalized temperature increase, and localized and/or generalized pain. Capillary dilatation and infiltration with leukocytes may be further characterized as edema (i.e., swelling) around the site of infection and/or damaged tissue. Inflammation may be an important mechanism for animals and humans to disable, destroy, and/or eliminate toxic particles or damaged tissue.

Those skilled in the art may appreciate that the immune system is a highly complex organization of cells and organs which are spread throughout the body. Moreover, two general divisions of immunity are commonly recognized by those skilled in the art. Natural (i.e., innate or native) immunity may be largely dependent on the complement system, phagocytes and cytokines to protect the body from infection. Animals and humans may be born with natural immunity which is encoded into genes.

Complement may be a group of related proteins that assist natural immunity cells and antibodies in recognizing (i.e., a cognitive phase) antigens or foreign particles. Complement proteins may bind to the surface of an antigen or foreign particle (i.e., activation phase). Activation by complement proteins may increase the membrane porosity of the antigen or foreign particle, which in turn may lead to disabling the antigen or foreign particle or, in the alternative, may serve as a "tagging" mechanism to enhance identification of the antigen or foreign particle by other natural immunity cells (e.g., phagocytes) and/or antibodies. Natural immunity cells and/or antibodies may then disable and/or eliminate the antigen or foreign particle (i.e., effector phase).

Phagocytes may belong to a group of cells which engulf and destroy other cells or particles through a process commonly referred to as phagocytosis. In addition, phagocytes (e.g., macrophages, neutrophils, natural killer cells) may secrete soluble mediators, commonly referred to as cytokines, which may be active in disabling and/or destroying an antigen or foreign particle. Cytokines may include for example, and not by way of limitation, interferons (e.g., α- and β-interferons), tumor necrosis factors (TNF), and interleukins.

Specific (i.e., acquired) immunity may retain the use of cells and molecules of natural immunity and may add two additional immune defense features. Specific immunity may provide a host (i.e., animal or human) with the ability to "remember" a specific antigen or foreign particle. This memory property may allow the host to mount a more effective defense upon each subsequent encounter with the specific antigen or foreign particle. Vaccination may be based upon the property of specific immunity to remember a specific antigen or foreign particle.

Specific immunity may also provide a host with the ability to "amplify" a natural immunity defensive response to an antigen or foreign particle. Moreover, the amplification process may also involve more accurate targeting of natural immunity to the site of entry for an antigen or foreign particle.

In addition, specific immunity may utilize a cognitive phase where specific antigens or foreign particles may be identified; an activation phase where specific antigens or foreign particles may be tagged; and an effector phase wherein specific antigens or foreign particles may be acted upon by an antibody, lymphocyte, or lymphocyte-derived cytokine to effectively disable and/or destroy the antigen or foreign particle.

Natural and specific immunity may be different in that complement and phagocytes are unable to distinguish different antigens and may not be enhanced in numbers following exposure of the host to the antigen or foreign particle. Whereas antibodies and lymphocytes may be able to identify specific antigens or foreign particles and may undergo an amplification in number following exposure of the host to the antigen or foreign particle.

Two classifications of specific immune responses may be recognized depending on which components of the immune system are being utilized. Humoral immunity may refer to the action of antibodies and other molecules which eliminate and/or neutralize antigens. Cell-mediated immunity (CMI), sometimes referred to as cellular immunity, may refer to the action of lymphocytes (e.g., B-lymphocytes ("B-cells") and T-lymphocytes ("T-cells")), in eliminating and/or neutralizing antigens or foreign particles.

Those skilled in the art will appreciate that endocrine and hormonal regulation of the immune system may involve a complex process. A plurality of hormones and hormonal pathways may be involved in immune system regulation. Important endocrine glands in immune regulation may include for example, and not by way of limitation, the pineal gland, hypothalamus, pituitary gland, and adrenal glands. The pineal gland may be responsible for the synthesis of melatonin from serotonin. Melatonin may have multiple effects on the body, which may include stimulating and/or enhancing the function of leukocytes and/or lymphocytes in response to an antigen or foreign particle. Serotonin may also have a positive effect on the immune system by stimulating the proliferation of T-cells and may enhance the function of certain phagocytes (e.g., macrophages).

The hypothalamus, pituitary, and adrenal glands form an important hormonal feedback pathway the, hypothalamic-pituitary-adrenal (HPA) axis, for regulating the response of the body to stress. The hypothalamus may secrete hormones which may act upon the pituitary gland causing it to release its hormones. Hormones from the pituitary gland may have actions on endocrine or other organs in the body. The adrenal glands may be responsible for producing a plurality of steroid hormones, including glucocorticoids, mineralocorticoids, and androgens. The adrenal glands may also be responsible for producing catecholamine hormones (e.g., epinephrine, norepinephrine, dopamine, and the like).

The higher incidence of infectious diseases in humans and animals subjected to stressful situations may be a result of the neuroendocrine and immune changes that occur during a challenging period. These changes may be the result of adaptation to the stressful situation. A widely investigated physiological and anatomical component of this process of adaptation to stress is the HPA axis. Activation of the HPA axis usually results in the elevation of glucocorticoid levels associated with stress, illness, and injury. Glucocorticoids may have suppressive effects on immune function and may play a role in stress-associated immune suppression. Immunosuppressive effects of glucocorticoids may therefore include reduction in the production of and/or destruction of immune system cells and suppression of inflammation by the immune system. In addition, adrenal catecholamines (e.g., epinephrine and norepinephrine) may be elevated in response to stress, and may have a prominent role in stress-related emotional states, including anxiety.

Albeit with structural similarities to melatonin, 6-MBOA and related compounds may function as melatonin agonists and at the α- and β-adrenergic cell receptors in their own right. Whereas melatonin exacerbates symptoms of dysphoria in depressed people, 6-MBOA and related compounds of the present invention, as a melatonin agonist, works in contrary fashion and actually stimulates a better mood.

As melatonin agonists, novel compounds of the present invention may stimulate the production of melatonin or may enhance the actions of melatonin on the immune system. For example, and not by way of limitation, 6-MBOA and related compounds of the present invention may stimulate the production of lymphocytes and the production of cytokines by immune system cells.

There has previously been no suggestion to implicate the administration of 6-MBOA and related novel compounds of the present invention in preserving and/or augmenting immune system function and/or reducing anxiety and related comorbidities, except for depression. To this end, the inventors of the present invention have found that calming and reducing symptoms of anxiety may be accomplished through use of the novel compounds of the present invention to stimulate serotonin- and melatonin-induced effects on the immune system and/or reduction of stress-induced neuroendocrine products.

In addition, serotonin and melatonin both may have immunoregulatory properties. Serotonin may enhance cell proliferation and macrophage antigen presentation. Melatonin may have enhancing activities in a number of stress-induced immune dysfunction models, including, but not limited to, restraint stress, injury, and cortisol administration. Moreover, as appreciated by those skilled in the art, 6-MBOA or related compounds of the present invention may be structurally and/or functionally similar to melatonin and catecholamines (e.g., epinephrine, alpha- and beta-adrenergic compounds, and the like), respectively.

6-MBOA or related compounds of the present invention may have both inhibitory and stimulatory effects in and around the central nervous system. As a melatonin analog, 6-MBOA may work at melatonin receptors as a melatonin antagonist, thus blocking the negative effects of melatonin on sexual maturation and/or function. In addition, the beta-adrenergic receptor effect of 6-MBOA may help to desensitize melatonin receptors and thus minimize the negative effects of melatonin on sexual maturation and/or function. Therefore, work by the inventors demonstrate that presently preferred embodiments of the compounds of the present invention possess some of the positive effects of melatonin function (e.g., calming and/or anti-anxiety effects and preserving and/or augmenting immune function) without stimulating the negative effects of melatonin action (e.g., inhibiting sexual maturation, dysphoria, and the like).

One presently preferred embodiment of a novel method of the present invention for the prevention or treatment of anxiety disorders and related behaviors and states involves administering to an animal or human in need of such treatment an effective amount of a compounds described in present application. There are several distinct anxiety disorders and related behaviors and states, including for example and not by way of limitation:
   Panic Disorder
   Agoraphobia
   Generalized Anxiety Disorder (GAD)
   Specific Phobia
   Social Phobia
   Obsessive-Compulsive Disorder (OCD)
   Post-Traumatic Stress Disorder (PTSD)
   Acute stress disorder
   Attention-Deficit Hyperactivity Disorder (ADHD)

The diseases described above as well as other anxiety disorders are classified in the Diagnostic and Statistical Manual of Mental Disorders, 4th Version, published by the American Psychiatric Association (DSM-IV). It is contemplated, however, that the spirit and scope of the present invention includes all anxiety conditions and comorbid conditions.

Anxiety disorders may be the most common type of human psychiatric disorder in the United States. Anxiety disorders may include, for example and not by way of limitation, panic disorder, obsessive-compulsive disorder, post-traumatic stress disorder, specific phobia, social phobia, and generalized anxiety disorder. Anxiety disorders may be characterized by uneasiness, fearfulness, and distress, sometimes experienced without clear evidence of real threats. During situations that are stressful, humans and animals may respond with alterations in behavior and autonomic and hormonal functions and secretions. These responses may result in exacerbation of anxiety symptoms during situations of stress, affecting mental and physical health and performance. Increased arousal during periods of anxiety may result in hypervigilance, increased startle response, impaired concentration and learning, insomnia, irritability, all of which may lead to decreased performance in a variety of settings in humans and animals. Millions of people in the United States (i.e., greater than 23 million diagnosed) may suffer from these conditions with significant costs to individual performance and health, lost productivity, and costs of treatment.

Performance and health of animals may often be challenged and detrimentally affected by anxiety behaviors. Anxiety provoking situations of novel environments, shipping and transport, illness or injury, weaning, crowding, castration, vaccination, dipping, deworming, tagging, branding, shoeing, and other processing procedures including training and performance may have detrimental effects on health, growth, and performance. Extensive effort in training individual animals to reduce anxiety is costly and often may not be practical. Similarly, loss of weight due to anxiety related stress conditions may result in heavy financial loss to the animal industry.

Currently available methods for treating anxiety disorders may include, for example and not by way of limitation, psychologic therapy, including behavioral, cognitive and emotive, and relaxation techniques, or training in animals. These methods may involve a significant amount of time and expense to achieve reduction in anxiety and enhancement of performance. Medications may also be used in humans and animals to reduce anxiety, including, for example and not by way of limitation, serotonin reuptake inhibitors (i.e., fluoxetine, paroxetine, sertraline, citalopram, escitalopram, fluvoxamine, venlafaxine, etc.), benzodiazepines (e.g., alprazolam, chlordiazepoxide, clorazepate, diazepam, halazepam, lorazepam, oxazepam, etc.), beta-blockers (i.e., beta-adrenergic receptor antagonists (e.g., propranolol, etc.), monoamine oxidase inhibitors (e.g., phenylzine, tranylcypromine, etc.), azapirones (e.g., buspirone), diphenylmethanes (e.g., diphenhydramine, hydroxyzine, etc.), and tricyclic antidepressants (e.g., amitryptyline, clomipramine, doxepin, imipramine, trimipramine, desipramine, nortriptyline, protriptyline, etc.). These medications may have serious side effects may not be easily accessible for the treatment of animals, and may be inappropriate for food production species. Therefore new methods for treating anxiety disorders are needed for both humans and animals.

The present invention provides novel compositions and methods for the prevention or treatment of anxiety disorders which involves administering to an animal or human in need of such treatment an effective amount of a compound described in this application. In addition, behaviors and negative consequences in animals related to anxiety may include, for example and not by way of limitation: (1) repetitive, compulsive and stereotypic actions (e.g., licking skin to ulceration, cribbing, sucking air, pacing, and other pathologic behaviors); (2) fear and phobias related to handling (e.g., loading into trailers, being touched, training, performance); (3) weaning stress; (4) social stress/mixing novel animals; (5) transportation; (6) confinement and crowding with associated weight loss and negative health effects; and (7) in food production animals (i.e., poor meat quality due to stress responses). Any of these disorders may be treated or prevented by the method and compounds of the present invention. Further, stressful situations that may place individual humans into novel, challenging, or threatening positions may also elicit anxiety symptoms and related behaviors and the present invention may minimize detrimental effects of such anxiety producing situations and enhance recovery, and may also prevent or minimize establishment of longer term anxiety disorders. Effective treatment of anxious humans and animals may aid in learning, training, and performance and may minimize or prevent detrimental physical consequences of stress and anxiety.

While past research by those skilled in the art has attempted to isolate, identify, and characterize new plant compounds with immune system, anti-anxiety and mood stimulating properties, 6-MBOA and are related compounds of the present invention have heretofore previously not been identified or evaluated for preserving and/or augmenting innate immune defenses and/or stimulating mood. Therefore, as readily appreciated by those skilled in the art, novel compounds derived, isolated, extracted, produced, and/or harvested from monocotyledonous plants and methods for using the same to preserve and/or augment innate immune defenses in humans and animals would be a significant advancement in the art. Such novel compositions and methods are disclosed and taught herein.

While past research by those skilled in the art has attempted to isolate, identify, and characterize new plant compounds with calming and/or anti-anxiety properties, 6-MBOA has not heretofore been identified or evaluated for calming or reducing anxiety. The novel compounds derived, isolated, extracted, produced and/or harvested from monocotyledonous plants or, in the alternative, by chemical synthesis and methods for using said compounds to calm and/or reduce anxiety and related comorbid behaviors and states in animals and humans as contemplated by the present invention is therefore a significant advancement in the art.

The following examples will illustrate the practice of the present invention in further detail. It will be readily understood by those skilled in the art that the following methods, formulations, and compositions of novel compounds of the present invention, as generally described and illustrated in the Example herein, are to be viewed as exemplary of the principles of the present invention, and not as restrictive to a particular structure or process for implementing those principles. Thus, the following more detailed description of the presently preferred embodiments of the methods, techniques, formulations and compositions of the present invention, as represented in Examples 1-17, is not intended to limit the scope of the invention, as claimed, but is merely representative of presently preferred embodiments of the invention.

Example 1

The Similar Physiological Effects of the Compounds of the Invention

Representative compounds of Formulas I, II, and III are shown below as compounds 1-7. The compounds of Formulas I, II and III have like physiological properties, and as such may be considered as similar or equivalent for therapeutic purposes, and were tested via a rodent model.

1. 2-amino-5-methoxyphenol [Member of Formula I]

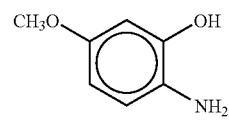

2. 6-methoxy-2-benzoxazolinone [Member of Formula II]

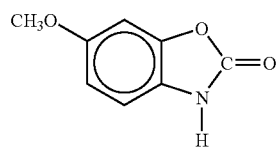

3. 2,4-dihydroxy-7-methoxy-1,4-(2H)-benzoxazin-3-one [Member of Formula III]

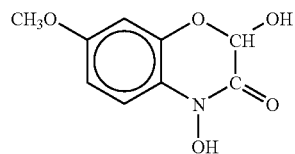

4. 2-hydroxy-4-methoxyacetanilide [Member of Formula I]

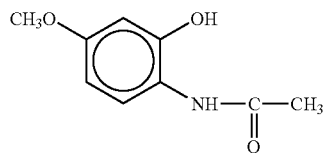

5. 2-hydroxy-4-ethoxyacetanilide [Member of Formula I]

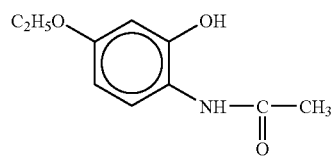

6. 5-methoxy-2-benzoxazolinone [Member of Formula III]

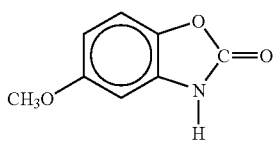

7. 2-hydroxy-5-methoxyacetanilide [Member of Formula I]

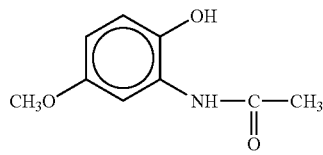

Female montane voles, *Microtis montanus*, received intra peritoneal injections of representative compounds belonging to Formulas I, II and III for three consecutive days and sacrificed twenty-four (24) hours after the last injection to examine uterine weight response. To assess the properties of each representative compound, pure ones made by chemical means (University of Utah Department of Chemistry, Salt Lake City, Utah) were prepared specifically for this test. All compounds were injected at a dose level of 5 mcg/day, dissolved in five percent (5%) propylene glycol for a total injection volume of 0.5 ml. Control animals received 0.5 ml of five percent (5%) propylene glycol only. All voles were 4-5 weeks old and weighed 25-29 g.

As illustrated in Table 1 below, all compounds belonging to Formulas I, II and III caused a statistically significant increase in uterine weights.

TABLE 1

Effect of injecting compounds of the invention, members of Formulas I, II and III on uterine weight in the montane vole, *Microtus montanus*.

| Compound Injected | Formula Numeral | Number of Animals | Average Uterine Weight (mg) |
|---|---|---|---|
| Control (Propylene Glycol) | — | 8 | 15.2 ± 2.4 |
| 6-methoxy-2-benzoxazolinone | II | 11 | 27.7 ± 5.6* |
| 5-methoxy-2-benzoxazolinone | III | 8 | 20.0 ± 4.7** |
| 2-hydroxy-4-methoxyacetanilide | I | 8 | 23.1 ± 2.7* |
| 2-hydroxy-4-ethoxyacetanilide | I | 8 | 22.2 ± 3.9* |
| 2-amino-5-methoxyphenol | I | 8 | 21.8 ± 3.5* |
| 2-hydroxy-5-methoxyacetanilide | I | 8 | 21.1 ± 4.4*** |
| 2-amino-4-methoxyphenol | I | 8 | 22.2 ± 3.2* |

*Significantly different from control at $P < 0.001$
**Significantly different from control at $P < 0.015$
***Significantly different from control at $P = 0.004$ On average, the uterine weight in voles receiving these was 22.8 g, fifty percent (50%) greater than for the control group. The greatest average weight increase, eighty-two percent (82%) more than the uterine weight for the control voles, was in those females administered 6-methoxy-2-benzoxazolinone, but even the least effect of a compound belonging to Formulas I, II or III, that for 5-methoxy-2-benzoxazolinone, entailed a thirty-two percent (32%) increase in uterine weight. The results show that physiological effects or modes of action are held in common by the compounds of the invention.

Example 2

Compounds of the Invention as an Antidepressant and Aphrodisiac in Human Males

This component of the invention relates to a method for lessening depression and otherwise bettering mood or feelings of well-being, said method comprising the administration to human males of an effective amount of one or more of the compounds of the invention defined herein. This component of the invention also relates to a method for treating sexual dysfunction or otherwise increasing sexual desire and performance, including but not necessarily limited to lacking interest in sex, problems with arousal, not enjoying sex, and anxiety about sexual performance, said method comprising the administration of an effective amount of one or more of the active compounds of the invention.

A double-blind crossover study was done on human males to test compounds of the invention as a therapeutic agent for treating depression or otherwise elevating mood as well as bettering sexual function. The trial had three phases, each two weeks in duration, during which participants took compounds of the invention for one phase or two weeks. The daily dose was made up from compounds of the invention naturally contained in the ground leaves from immature corn plants, 30-45 cm tall, standardized with synthesized 6-methoxy-2-benzoxazolinone, to a total of 15 mg 6-methoxy-2-benzoxazolinone. A dose of fifteen milligrams (15 mg) was selected because this was considered a likely minimum effective daily amount for humans, extrapolated from prior studies on rodents, rabbits and other animals. Previous anecdotal trials on humans done by the inventors suggested that a 15 mg daily dose had a desirable effect, but no adverse consequences to health. In general, therapeutically effective amounts of compounds of the invention may be found in a daily dosage range of between about 5 micrograms (mcg) to about 60 mg.

Weekly assessments of depression or mental well being and sexual function were done via widely accepted indices: to quantify depression and generalized anxiety disorders, the Hospital Anxiety and Depression Scale (HAD); and for sexual desire, psychological arousal, and overall sexual outlook, the Arizona Sexual Experience Index (SEX).

Phase One lasted 14 days, during which participants took daily doses of the invention or a placebo. Assignation of the invention or placebo to male participants was done randomly. Immediately prior to the 14 days comprising Phase One, an initial physical examination and blood analysis were done. At that time, each male filled out HAD and SEX forms to assess mental well being and sexual function, was checked for sitting and standing blood pressure and pulse, and gave the blood sample needed for the biochemical analyses.

Phase Two consisted of a seven-day period immediately after Phase One, during which neither invention nor placebo was taken. During Phase Two, physical examination and laboratory analyses were again done. In Phase Three which lasted 14 days, participants again took either invention or a placebo. Assignation of the invention or placebo was done according to the sort of capsule taken during Phase One. If a participant took a compound of the invention in Phase One, then placebo was administered during Phase Three, and vice versa. Immediately after finishing Phase Three, a physical examination and laboratory analyses were again done. After completing Phase Three, each participant was asked prepared questions as well as solicited for any comments and impressions concerning invention use.

Table 2 is a tabular summary of a presently preferred embodiment of results that may be observed in Example 2.

TABLE 2

HAD and ASEX summaries for administration of
the compounds of invention to adult males.

| Participant | With Compounds of Invention: | | With Placebo: | |
|---|---|---|---|---|
| | Initial Value | After Two-Weeks | Initial Value | After Two-Weeks |
| 1 | 9.0, 12.0 | 8.0, 11.0 | 8.0, 10.0 | 8.0, 13.0 |
| 2 | 16.0, 13.0 | 14.0, 12.0 | 16.0, 13.0 | 16.0, 15.0 |
| 3 | 15.0, 10.0 | 9.0, 11.0 | 15.0, 14.0 | 17.0, 14.0 |
| 4 | 12.0, 9.0 | 7.0, 10.0 | 9.0, 10.0 | 9.0, 12.0 |
| 5 | 14.0, 10.0 | 10.0, 10.0 | 12.0, 10.0 | 14.0, 10.0 |
| 6 | Participant not reliable - Data incomplete and deleted from study | | | |
| 7 | 12.0, 9.0 | 7.0, 9.0 | 9.0, 10.0 | 8.0, 9.0 |
| 8 | 12.0, 11.0 | 8.0, 11.0 | 12.0, 11.0 | 12.0, 10.0 |
| 9 | 12.0, 15.0 | 12.0, 10.0 | 7.0, 10.0 | 7.0, 10.0 |
| 10 | 4.0, 15.0 | 0.0, 13.0 | 9.0, 12.0 | 12.0, 12.0 |
| 11 | 21.0, 10.0 | 6.0, 10.0 | 9.0, 12.0 | 12.0, 12.0 |
| 12 | 13.0, 9.0 | 2.0, 9.0 | 13.0, 9.0 | 13.0, 9.0 |
| 13 | 14.0, 12.0 | 13.0, 10.0 | 12.0, 10.0 | 12.0, 10.0 |
| 14 | 12.0, 10.0 | 13.0, 10.0 | 18.0, 7.0 | 16.0, 7.0 |
| 15 | 23.0, 8.0 | 18.0, 9.0 | 16.0, 9.0 | 16.0, 8.0 |
| Average | 13.5, 10.9 | 9.1, 10.4 | 11.8, 10.5 | 12.3, 10.8 |

The HAD value precedes the ASEX one, and these are separated from each other by a comma.
Two-Sample Paired Sign Test - This is one of the stronger or more reliable statistical tests when significance is detected. The question is whether INVENTION affects feelings of well-being or sexual function. The Sign-Test is used to statistically ask "how often compounds of invention impact feelings of well being and/or sexual function". Results are as follows:
HAD (with invention), $p < 0.003$, Very Significant
ASEX (with invention), $p < 0.727$, Not Significant
HAD (with placebo), $p < 0.688$, Not Significant
ASEX (with placebo), $p < 1.310$, Not Significant These data indicate that the compounds of the invention have significant positive effect on depression or mood. Fourteen (14) of the fifteen (15) participants properly completed the study and only data for these individuals were used for analysis. HAD scores exceeding 20.0 denote clinical depression, but lower ones can also be associated with dispirited mood. Only two males entered the trial with HAD values exceeding the clinical minimum (21.0 and 23.0). Still, twelve (12) of fourteen (14) subjects showed bettered mood, improved feelings of well being or lessened depression after taking compounds of the invention. Decreases in HAD scores over the two-week timespan were as much as 15 and averaged 5.2. The two clinically depressed subjects showed decreases in HAD values of 5.0 and 15.0. The average HAD score went from 13.5 at the onset of the study to 9.1 after two weeks of taking compounds of the invention, very significant statistically. Participants showed no statistically detectable changes while taking placebo.

After taking compounds of the invention for two weeks, five (5) of fourteen (14) participants had lessened ASEX values, indicating improved sexual response or lessened sexual anxiety, while only two (2) of fourteen (14) males showed the same after two weeks on placebo. Statistical significance was not found for the ASEX changes, but such could be attributed to a small sample size. Sexual benefits of the compounds of the invention were also obviated in the trial through the exit interviews given to all participants. While taking these, a majority of males reported morning erections of the penis greater in size, duration or frequency than usually experienced when not taking the compound. Also, comments by the majority centered about feeling "like a teenager" (direct quote) in terms of energy, sexual and otherwise. It should be noted that personal situations were complicated by unwilling or lacking sex partners. Twelve (12) of fifteen (15) participants also expressed an unsolicited desire to continue using the compounds of the invention. They stated a belief that the compounds of the invention could prove useful to them in a sexual context.

Example 3

Compounds of the Invention as an Antidepressant in Human Females

This example further relates to a method for lessening depression and otherwise bettering mood or feelings of well-being, said method comprising the administration to human females of an effective amount of the compounds of the invention, defined above. Compounds of the invention were used to treat eight females with clinical depression, which for three females had been ongoing for at least one year. Participants took the same dose of compounds of the invention as in Example 2, 15-mg each day. A HAD was administered to participants prior to beginning daily doses. Each participant was interviewed every two weeks to check for adverse side effects and for comments on use of the compounds of the invention. A HAD Index was again administered upon completion of the six-week trial.

Referring Table 3, one presently preferred embodiment of the results of the study are tabulated.

TABLE 3

HAD summary for clinically-depressed females taking
compounds of the invention for six weeks.

| Participant[1] | Initial Value | After Six-Weeks |
|---|---|---|
| 1 | 23.0 | 18.0 |
| 2 | 21.0 | 8.0 |
| 3 | 21.0 | 21.0 |
| 4 | 24.0 | 14.0 |
| 5 | 22.0 | 12.0 |
| 6 | 21.0 | 13.0 |
| 7 | 23.0 | 7.0 |
| 8 | 20.0 | 22.0 |
| Average | 21.9 | 14.4 |

[1]Participants 1-4 initially [Weeks 1-2] were given compounds of invention under guise of its being a vitamin/mineral mixture.
Two-Sample Paired Sign Test - This is one of the stronger or more reliable statistical tests when significance is detected. The question is whether compounds of invention affect depression or feelings of well-being. The Sign-Test is used to statistically ask "how often compounds of invention positively impact depression or feelings of well being". Results are as follows:
HAD, $p < 0.0313$, Significant These data indicate that the compounds of the invention significantly lessen depression. Initial HAD scores exceeded 20 for all subjects. All females were clinically depressed, and their HAD scores averaged 21.9. Six (6) of eight (8) participants showed responses to compounds of the invention in which HAD values decreased 5-16 points, an average decrease of 10.5 over the six-week timespan. The overall average HAD score decreased from 21.9 (clinically depressed) at trial onset to 14.4 (not clinically depressed) after six weeks of use, with two participants ending with HAD values of eight (8) and seven (7). There were only eight females in the trial, but decreases in HAD scores were still statistically significant ($p<0.031$). The antidepressant properties of the compounds of the invention are obviated.

Both excess weight and substance abuse are characterized by either primary or secondary depression. Since such psychological factors affecting excess weight and substance abuse must be treated along with the physiological ones for therapies to be effective in the long term, the compounds of the invention comprise adjunctive treatments for achieving weight loss or reducing the risk of relapse in persons with substance abuse or addiction problems.

Example 4

Compounds of the Invention at Concentrations Suitable for Human Therapies from Plants Harvested and Processed in Unique Fashion Example 4 relates to a method for obtaining compounds of the invention at concentrations suitable for human therapies from plants grown to an immature stage of growth. "Concentrations suitable for human therapies" means that compounds of the invention in ten (10) grams or less of dried plant material make up a daily dose (e.g., fifteen (15) mg compounds of the invention as 6-methoxy-2-benzoxazolinone; however, general therapeutically effective daily dosages of compounds of the invention may be between about five (5) mcg to about sixty (60) mg). Said dosage may include either the novel compound as it naturally occurs or synthetically, or a combination of both natural and synthetic novel compounds of the present invention.

Specific harvesting and drying conditions are specified herein, as are analytical parameters for determining crop quality. By "specific harvesting and drying conditions", it is meant that compounds of the invention are obtained from plants via circumstances differing from the usual manner in which the plants are handled for the terminal product.

As an example, corn, *Zea mays*, is typically grown to its adult or matured states for its seed-laden cob. At the immature growth stage at which compounds of the invention occur, corn plants have a biomass that portends harvest of a substantial amount of leaf material containing the compounds of the invention at concentrations suitable for human therapies. Hence, dried corn leaves from immature plants become appropriate for the human therapies elucidated herein, or the dried leaves are a resource for the concentration, extraction and purification of the compounds of the invention. There are other monocotyledonous plants with the natural production of compounds of the invention at concentrations suitable for human therapies.

Monocotyledons are flowering plants whose embryo has only one cotyledon, or seed leaf. The monocotyledons are a monophyletic group (i.e., derived from a single ancestral line) encompassing, but not limited to the following botanical families: Poaceae (true grasses, alternately referred to as Gramineae), Acoraceae (sweet flag), Agavaceae (yuccas), Alismataceae (water plantains), Anemarrhenaceae (zhi mu), Anthericaceae (slender grass lily), Araceae (arum lilies), Asparagaceae (asparagus), Behniaceae (paleotropical lianas), Bromeliaceae (bromeliads, pineapple), Butomaceae (flowering rushes), Calamoideae (palms or palm trees), Colchicaceae (milkmaids), Commelinaceae (blue gingers), Cymodoceaceae (shoalweed, surfgrass, widgeonweed), Cyperaceae (cotton grasses, spike rushes, sedges), Dioscoreaceae (yams), Eriocaulaceae (hat pins, pipewort), Flagellariaceae (false rattan), Hydrocharitaceae (waterweed), Iridaceae (iris), Juncaceae (rushes, wood-rush), Juncaginaceae (arrow-weeds, arrow-grasses), Lanariaceae (soapwort, latherwort, scourwort), Lemnaceae (duckweeds), Liliaceae (lilies, onions, blubells), Lowiaceae (orchidantha), Marantaceae (arrowroot, maranta, prayer-plant), Mayacaceae (bog-moss, mayaca), Musaceae (banana), Nolinaceae (beargrass), Orchidaceae (orchids), Philydraceae (frogsmouth), Phormaiaceae (flax lily), Posidoniaceae (posidonias), Potamogetonaceae (pondweeds), Rapateaceae (rapatea), Restionaceae (olifantsriet, rekoala grass, sprucecones), Ruppiaceae (large-fruit tassel, widgeon grass), Sparganiaceae (bur-reeds), Themidaceae (ookow, Bridges' triteleia), Thurniaceae (prionium, thurnia), Typhaceae (bulrushes), Xyridaceae (yellow-eyed grass), Zingiberaceae (ginger), and Zosteraceae (eel grass). It is contemplated that compounds of the invention may be derived isolated, harvested and/or extracted from plants selected from any of the above identified or other monocotyledonous plant families or plant orders.

Preferred embodiments of the compounds of the invention may be selected from families of Cyperaceae and Poaceae (alternately referred to as Graminae). Species therein include the cereal grasses (e.g., sorghum, corn or maize, wheat, rye, rice, barley and oats); species related to the cereal grasses like gamagrass (*Tripsacum* species), wild rice (*Zizania aquatica, Z. texana*) and teosinte (*Zea diploperennis, Z. luxurians*, wild *Z. mays, Z. nicaraguensis, Z. perennis*); sugarcane (*Saccharum* species); bamboo (including but not limited to species of *Bambusa, Bashania, Cephalostachyum, Dendrocalamus, Dinochloa, Fargesia, Gigantochloa, Kinabaluchloa, Melocalamus, Nastus, Phyllostchys, Schizostacyum, Sinarundinaria, Thyrsostachys, Vietnamosasa*, and *Yushania*); and pasture grasses (including but not limited to annual ryegrass, bent grass, Bermudagrass, bluegrass, kleingrass, orchard grass, ribgrass, Sudangrass, timothy grass and fescue); along with wild grasses (including but not limited to alkaligrass, bluestem grass, buffalograss, dallisgrass, hairgrass, Indiangrass, lovegrass, meadow grass, napiergrass, pampas grass, pangolagrass, panicgrass, rabbitsfoot grass, slender wild oats, switchgrass, toothbrush grass, wheatgrass); millet (including but not limited to plants in the genera *Panicum, Setaria, Echinochloa, Pennesetum* and *Eleusine*); Job's tears (*Coix lachryma-jobi; Coix aquatica*); and the barley-like grasses (including but not necessarily limited to species of *Hordeum, Setaria, Astrebla, Isolepis, Luzula* and *Hyparrhenia*).

Growing corn to obtain the compounds of the invention is initially done in a conventional fashion, but seeds are planted more densely than is the case for conventional crops because of the smaller size of plants at harvest. Harvest time is done while plants are immature. For corn, this immature plant harvesting may happen when plants are no more than about thirty (30) to about forty-five (45) centimeters tall, about five weeks after planting. Preferably, embodiments of the invention may also utilize harvesting immature corn plants that are between about forty-five (45) centimeters to about 122 centimeters in height, and between about five weeks to about eight weeks after planting are sought and preferably less than ten weeks. As a general reference, mature corn plants are typically more than 180 centimeters in height and are grown for about four (4) to about five (5) months after planting. For corn, harvesting is preferably done by cutting plants at 3-4 centimeters above the ground. Severed plants may be gathered and may be dried at temperatures held at about 40° Celsius (C) to about 45° C. Empirical studies showed that this temperature range helps maximize conversion of the precursors of compounds of the invention to the active molecules.

In a trial plot in southern Illinois, approximately 38,000 corn plants yielded 137 kilograms (300 pounds) of dried (96% dry weight) corn leaves with suitable levels of compounds of the invention. Analyses via mass spectroscopy showed that substantive amounts of the compounds of the invention were in dried corn leaves after five (5) weeks of growing time. Five (5) random samples of dried corn leaves were obtained for analysis. For each dried corn leaf sample, a one-gram portion was homogenized in 10-ml distilled water, incubated at 25° C. for one (1) hour, boiled for thirty (30) min, and then centrifuged for ten (10) min at 3600 rpm. The resulting supernatant was extracted three (3) times with ten (10) ml reagent-grade dichloromethane per extraction. The three (3) extracts were combined and allowed to air dry, after which the dried residue was stored in a tightly stoppered glass tube.

The dried residue was analyzed for 6-MBOA by gas-chromatographic mass spectroscopy. A Dupont Model DP102 device with an integrator and a SP2250 GC column isothermal at 200° C. (Dupont, Wilmington, Del.) was used. A standard curve for 6-MBOA was obtained using 0.06-, 0.60- and 1.20-.mu.g injections of pure, synthetic 6-MBOA (Sigma, Saint Louis, Mo.) in methanol solution and was reproducible at a five percent (5%) level.

6-MBOA occurred in dried corn leaves at levels suitable for human consumption. Samples averaged ten (10) mg/g 6-MBOA, with individual samples assaying as follows: eight (8), nine (9), ten (10), ten (10), and twelve (12) mg/g 6-MBOA, respectively. At such concentrations, less than two (2) grams dried corn leaves are needed to make up a daily human dose. This makes corn leaves, as uniquely grown, harvested and dried herein, a suitable source of compounds of the invention. For comparison purposes, leaves from plants grown more than eight (8) weeks were analyzed for 6-MBOA. Virtually none was present.

Previous work by the inventors indicated that higher levels of the compounds of the invention are associated with multiple biochemical parameters that indicate crop quality or adequacy with respect to the compounds of the invention. In those plants containing compounds of the invention at concentrations suitable for human use total phenols are at concentrations greater than 17.0 mg/gm (dry weight) but combined amounts of 4-hydroxycinnamic acid and 4-hydroxy-3-methoxycinnamic acid total no more than 1.5 mg/gm (dry weight), as determined through chromatography. For invention, the above mentioned parameters for total phenols and combined amounts of 4-hydroxycinnamic acid and 4-hydroxy-3-methoxycinnamic acid are instituted here as elements of the invention as it pertains to plants. For the corn leaf samples of Example 2, total phenols averaged 19.1 mg/gm and the cumulative total for cinnamic acids averaged 0.9 mg/gm.

Example 5

Compounds of the Invention from Parts of Animals

The main food of deer and elk (Cervidae) for most of the year is browse, the growing tips of low-growing, woody plants. However, casting of hard antlers from the previous year coincides with a spring flush in natural pasturage and an accompanying shift to a diet of grasses, chiefly sprouting and immature ones. Such grasses are at developmental stages in which 6-MBOA and related compounds are most prevalent.

After casting, new antlers begin their development. These growing antlers are nourished by blood vessels from a covering of skin, called velvet. An antler grows from the tip with tissue laid down as the tip advances. A velvet antler tip has a soft cartilaginous internal structure and high fat content, contrasting the rest of the antler with its ossified cartilage and little fat.

Air-dried and freeze-dried velvet antler samples were obtained. These came from commercially farmed Canadian Wapiti and New Zealand red deer, both subspecies of elk, *Cervus elaphus*. All animals had been maintained on grassy pasturage. The samples were from velvet antlers that had been growing fifty-five (55) to sixty-five (65) days, and included both tips, defined as the region five (5) cm or less in length starting at the apex, as well as other, more matured parts of the antler.

For each sample of dried antler, a one-gram portion was homogenized in ten (10)-ml distilled water, incubated at 25° C. for one (1) hour, boiled for thirty (30) min, and then centrifuged for ten (10) min at 3600 rpm. The resulting supernatant was extracted three (3) times with ten (10) ml reagent-grade dichloromethane per extraction. The three (3) extracts were combined and allowed to air dry, after which the dried residue was stored in a tightly stoppered glass tube.

The dried residue was analyzed for 6-MBOA by gas-chromatographic mass spectroscopy. A Dupont Model DP102 device with an integrator and a SP2250 GC column isothermal at 200° C. (Dupont, Wilmington, Del.) was used. A standard curve for 6-MBOA was obtained using 0.06-, 0.60- and 1.20-.mcg injections of pure, synthetic 6-MBOA (Sigma, Saint Louis, Mo.) in methanol solution and was reproducible at a five percent (5%) level.

Referring to Table 4, the observations of Example 5 may be summarized as follows:

TABLE 4

| 6-MBOA in Dried Velvet Antler from Elk, *Cervus elaphus*. | | | | |
|---|---|---|---|---|
| Animal | Origin | Tip or Other | Drying Method | 6-MBOA (mg/g dry weight) |
| Wapiti | Canada | Tip | Air | 2.5 |
| Wapiti | Canada | Tip | Air | 2.8 |
| Wapiti | Canada | Other | Air | 0.3 |
| Red Deer | New Zealand | Tip | Freeze | 1.9 |
| Red Deer | New Zealand | Other | Freeze | 0.5 |

These data indicate 6-MBOA was present in all tip samples, with little or none present in those from the more matured parts of the antler. Notably, amounts of 6-MBOA from velvet antler tips exceeded those typically found in grasses less than a week after sprouting, the stage of growth with the most 6-MBOA. These results show that ingested 6-MBOA is accumulated or concentrated in velvet antler tips, and as such represent a means for obtaining the compounds of the invention in concentrations suitable for human use.

Many animals eat grasses and other monocotyledonous plants. Such animals may also be accumulating compounds of the invention in body parts, most likely in those characterized by high fat contents. Obtaining compounds of the invention from body parts other than the antlers of elk and deer and from animals other than elk or deer are not precluded from invention.

Example 6

Alternative Embodiments of the Novel Compounds

Any number of alternative embodiments of precursors of phenolic compounds of the present invention may be contemplated as falling within the spirit and scope of the present invention. In particular, Formula V, below, is a general chemical formula depicting a generic representation of alternative preferred embodiments of precursors of phenolic compounds of the present invention.

Formula V—A compound according to the formula:

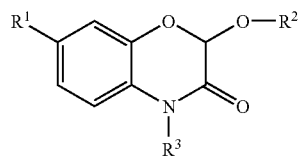

Wherein "$R^1$" is selected from the group consisting of H and $OCH_3$;

Wherein "$R^2$" is selected from the group consisting of H and Glucose (as a glucoside)

Wherein "$R^3$" is selected from the group consisting of H, OH, and $OCH_3$;

or pharmaceutically acceptable salts thereof.

As shown, such embodiments of novel compounds of the present invention may include benzoxazinoids-cyclic hydroxyamic acids, lactams and corresponding glucosides. As contemplated herein, substitution at the "$R^1$" position may be accomplished with a member selected from the group consisting of H and $OCH_3$. Substitution at the "$R^2$" position may be accomplished with a member selected from the group consisting of H and glucose (as a glucoside). Substitution at the "$R^3$" position may be accomplished with a member selected from the group consisting of H, OH, and $OCH_3$.

Referring now compounds 8-17 below, a series of chemical formulae, according to the generic representation shown in Formula V, illustrate chemical structures for representative compounds of further embodiments of novel compounds of the present invention.

8. 2,4-dihydroxy-1,4-benzoxazin-3-one (DIBOA)

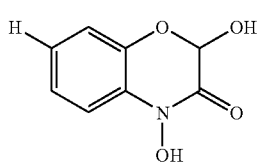

9. 2,4-dihydroxy-1,4-benzoxazin-3-one-glucoside (DIBOA-Glc)

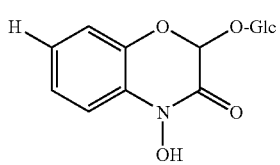

10. 2,4-dihydroxy-7-methoxy-1,4-benzoxazin-3-one (DIMBOA)

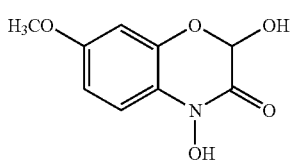

11. 2,4-dihydroxy-7-methoxy-1,4-benzoxazin-3-one-glucoside (DIMBOA-Glc)

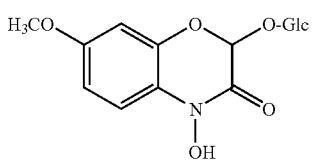

12. 2-hydroxy-1,4-benzoxazin-3-one (HBOA)

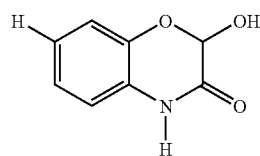

13. 2-hydroxy-1,4-benzoxazin-3-one-glucoside (HBOA-Glc)

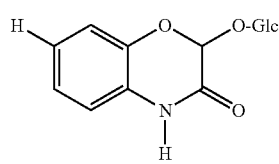

14. 2-hydroxy-7-methoxy-1,4-benzoxazin-3-one (HMBOA)

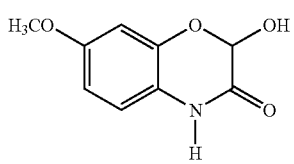

15. 2-hydroxy-7-methoxy-1,4-benzoxazin-3-one-glucoside (HMBOA-Glc)

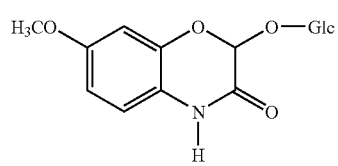

16. 2-hydroxy-4,7-dimethoxy-1,4-benzoxazin-3-one (HDMBOA)

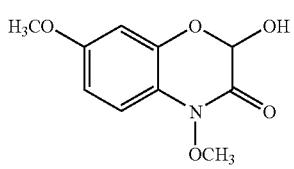

17. 2-hydroxy-4,7-dimethoxy-1,4-benzoxazin-3-one-glucoside (HDMBOA-Glc)

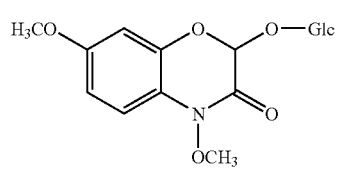

Specifically, compound 8 illustrates a chemical formula for 2,4-dihydroxy-1,4-benzoxazin-3-one (DIBOA). DIBOA may also have a glucose molecule to form a glucoside (also referred to as a glycoside), DIBOA-Glc, which is shown compound 9. As illustrated, compound 10 depicts a chemical formula for 2,4-dihydroxy-7-methoxy-1,4-benzoxazin-3-one (DIMBOA). DIMBOA may also exist in combination with glucose molecule to form a glycoside compound (DIMBOA-Glc), which is shown as compound 11.

Compound 12 illustrates a chemical formula for 2-hydroxy-1,4-benzoxazin-3-one (HBOA). A glycoside may also form between HBOA and a glucose molecule (HBOA-Glc) and is shown as compound 13. Compound 14 depicts a chemical formula for 2-hydroxy-7-methoxy-1,4-benzoxazin-3-one (HMBOA). HMBOA may also contain a glucose molecule to form HMBOA-Glc, which is depicted as compound 15. Additionally, compound 16, illustrates a chemical formula for 2-hydroxy-4,7-dimethoxy-1,4-benzoxazin-3-one (HDMBOA). Wherein, compound 17 illustrates an glucoside formed between HDMBOA and glucose (HDMBOA-Glc). In the foregoing examples, glucose molecules may be bonded to a respective aglycone (i.e., non-sugar) compound (e.g., DIBOA, DIMBOA, HBOA, HDMBOA, 6-MBOA) to form a glycoside.

As appreciated, glucose molecules typically are in the form of a pyranose (i.e., cyclic 6-carbon ring), which may be referred to as a glucopyranose. Glucopyranose compounds usually bond with the aglycone portion as an hemiacetal. Configurations of glycoside compounds in yet other presently preferred embodiments of the present invention may be found in the (2R)-configuration. It is intended, however, that other forms of glucose and configurations of glycosides are contemplated to be within the spirit and scope of the novel compounds of the present invention. The presently preferred embodiments of compounds of the present invention, as shown in Example 6, are intended therefore to be viewed as exemplary of the principles of the present invention, and not as restrictive to any particular formula, structure or method for implementing and/or practicing the present invention.

Example 7

Novel Compounds of the Invention in Preserving and/or Augmenting Innate Immune Defenses in Giant Pandas The endangered giant panda (*Ailuropoda melanoleuca*) is a bear-like mammal native to the high bamboo and pine forests of central China. The total number of giant pandas in the wild is now about 1,500, with another 140 animals housed in zoos and research centers. These numbers may place giant pandas as one of the most endangered species on Earth. One reason that giant panda populations may be at endangered levels is due to high infant mortality rates. Babies born in captive panda populations may have less than a fifty percent (50%) chance of survival to weaning. Of forty-two (42) giant pandas produced in captivity between 1980 and 1997, only twenty-three (23) have survived. It has been documented that giant panda babies usually die because of infectious disease and/or an immature immune system.

Wild giant pandas may primarily eat bamboo. Bamboo may be categorized as a monocotyledonous plant. Moreover, giant pandas occasionally eat flowers, vines, grasses, pine bark, honey, insects and rodents. Certain bamboo species may be widespread at the high altitudes that pandas may now inhabit. Species of bamboo may include, for example and not by way of limitation, *Fargesia spathacea, Sinarundinaria chungii, S. nitida*, and *S. fangiana*. All may invariably contain compounds in accordance with presently preferred embodiments of the present invention in the shoots and otherwise young leaves. There may be virtually none of the compounds of the present invention, however, occurring in the older life history stages of these bamboo plants.

In particular, compounds in accordance with presently preferred embodiments of the present invention that are found in bamboo are quite extant immediately prior to and during the breeding season. During such times, bamboo shoots and younger leaves, those states in which the compounds of the invention are particularly plentiful, may be preferentially eaten by giant pandas. Meanwhile, the matured or older bamboo leaves so prevalent at other times have little or none of compounds contemplated by the presently preferred embodiments of the present invention.

Adult giant pandas may consume between about twelve (12) to about fifteen (15) kilograms of food per day when feeding on matured or older bamboo leaves and stems. However, when feeding in nature on bamboo shoots, which have the compounds in accordance with presently preferred embodiments of the present invention, giant pandas may consume up to thirty-eight (38) kilograms per day. This may account for about forty percent (40%) of their average body weight.

Historically, the compounds of the present invention may almost always be lacking in zoo diets fed to giant pandas. Unlike the diet of wild pandas, captive animals are typically fed only older bamboo, with only minuscule amounts of the active compounds of the present invention. Captive pandas may also be fed rice gruel, carrots, apples, ground corn and sweet potatoes.

It has been previously demonstrated that the compounds in accordance with presently preferred embodiments of the present invention may be passed from giant panda mothers to offspring during gestation and/or lactation (Nelson, "Maternal diet influences reproductive development in male prairie vole offspring," Physiology of Behavior 50:1063-1066). Accordingly, female giant pandas who may be fed the active compounds of the present invention may be examined from the perspective of preweaning baby panda survival.

In this example, bamboo with a relative abundance of the compounds comprising the invention were fed to animals at the Giant Panda Breeding Center, Wolong Nature Reserve, Sichuan Province, China. There are more than forty (40) adult pandas at the Center, which accounts for thirty percent (30%) of the total number of captive pandas in the world.

Levels of the active compounds of the present invention may be determined for shoots, younger leaves emerging from the shoots and matured, older leaves of *Fargesia spathacea*, the most usual bamboo species fed at the Wolong Giant Panda Breeding Center. Three (3) samples of each developmental state of bamboo were taken and dried at 40-45° C. For each dried bamboo leaf or shoot sample, approximately a one-gram portion was homogenized in ten (10)-mL distilled water, incubated at 25° C. for about one (1) hour, boiled for about thirty (30) min and then centrifuged for about ten (10) minutes at approximately 3600 rpm. The resulting supernatant was extracted three (3) times with ten (10) mL reagent-grade dichloromethane per extraction. The three (3) extracts were then combined and allowed to air dry, after which the dried residue may be stored in a tightly stoppered glass tube.

The dried residue was analyzed for 6-methoxy-2-benzoxazolinone (6-MBOA) by gas-chromatographic mass spectroscopy. A Dupont Model DP 102 device with an integrator and a SP2250 GC column isothermal at 200° C. (Dupont, Wilmington, Del.) was used. A standard curve for 6-MBOA was obtained using 0.06-, 0.60- and 1.20-µg injections of pure, synthetic 6-MBOA (Sigma, Saint Louis, Mo.) in methanol solution and was reproducible at a five percent (5%) level.

6-MBOA contents (in parts per million) for the nine (9) *Fargesia spathacea* samples were, as follows: (1) Shoots=56, 88, 91; (2) Younger leaves=23, 27, 38; (3) Mature, Old Leaves=3, 3, 5.

During the 2003 Breeding Season—approximately March though May—captive pandas may receive a diet consisting chiefly of bamboo shoots and young leaves in the month prior to and also during the March through May reproductive period. Average consumption may be on the range of about twenty-eight (28) kilograms of bamboo per day over this time span. Rice and vegetable gruel may also be fed to the pandas. Older bamboo leaves are preferably precluded, as much as possible, in contrast to past breeding seasons when these encompassed most of the diet.

Prior to concerted efforts to feed bamboo at developmental states characterized by notable amounts of the compounds of the present invention, only ten percent (10%) of captive male pandas at the Breeding Center reproduced in a natural way, less than thirty percent (30%) of females gave birth and more than fifty percent (50%) of the panda babies died prior to weaning. Bamboo fed during previous reproduction seasons consisted chiefly of mature older plants. Indeed, older plant material may have been readily and cheaply obtainable in large amounts, so little or no younger material had been offered on a concerted basis let alone in quantity.

Based on the findings and research conducted at the Giant Panda Breeding Center, with bamboo containing the compounds in accordance with presently preferred embodiments of the present invention making up a large part of the diet, the birthrate increased about three-fold (3×), with almost all captive females achieving pregnancy. Baby survival past weaning, which had previously entailed a high mortality due to infectious disease, became almost total survival. Indeed, a record number of young were produced—nineteen (19) offspring—during this example in the 2003 Breeding Season at the Giant Panda Breeding Center. Of these offspring, two (2) had been stillborn and one (1) died quite soon after birth. Necropsy of the three (3) animals revealed nothing as to any problems of an infectious or pathogenic nature. The remaining offspring have continued to thrive through January 2004. In summary, unprecedented survival of giant pandas may be observed following administration of compounds of the present invention, in view of the normally expected greater than fifty percent (50%) infant mortality based on the outcome of previous reproductive seasons.

Example 8

Novel Compounds of the Invention in Preserving and/or Augmenting Innate Immune Defenses in Mice Study Design A model for examining stress-induced changes in animals may involve subjecting animals to a stressful environment for a desired period of time sufficient to suppress innate immune responses, then subjecting the animals to an agent known to precipitate an immune response (i.e., immunogenic or antigenic agent). Typically, the immune response may be measured by the amount of localized swelling (i.e., inflammation) that may occur near the administration site of the immunogenic agent. The effects of a particular immunogenic agent on the immune system of an animal may be examined by comparing the degree of swelling in control and experimental groups of the animals.

Male albino inbred strain mice, Balb/c (Charles River, Inc.), at about eight (8) weeks of age were used in the present exemplary study. As appreciated by those skilled in the art, Balb/c mice are often used in stress/injury testing because they may be more susceptible to stress and injury compared to other strains of animals and, importantly, immune system changes are more easily observed in these animals.

It is anticipated that the mice that are stressed, but also exposed to immature corn leaves containing 6-MBOA or related compounds of the present invention (i.e., stressed/6-MBOA mice) may have the ability to mount an immune response to a known immunogenic agent. In contrast, those mice that may be stressed, but not exposed to immature corn leaves containing 6-MBOA or related compounds of the present invention (i.e., stressed/non-6-MBOA mice) may have little or no ability to mount an immune response to a known immunogenic agent. Likewise, additional control groups may utilize mice that are not stressed, and are not exposed to immature corn leaves containing 6-MBOA or related compounds of the present invention (i.e., non-stressed/non-6-MBOA mice) and mice that are stressed, but are not exposed to immature corn leaves containing 6-MBOA or related compounds of the present invention (i.e., stressed/non-6-MBOA mice).

In the present study, twenty (20) Balb/c mice were evenly divided into four (4) groups. These groups comprised the following characteristics: Group 1 included a control group of non-stressed/non-6-MBOA mice; Group 2 included a group of stressed/non-6-MBOA mice; Group 3 included a group of non-stressed/6-MBOA mice and Group 4 included a group of stressed/6-MBOA mice.

Beginning on day 3 prior (Day −3) to exposure to a stress procedure, immature corn leaves containing 6-MBOA or related compounds of the present invention was administered to the mice in Groups 3 and 4 orally via feed. The mouse chow was chopped into small bits, followed by the addition of immature corn leaves containing 6-MBOA or related compounds of the present invention at an appropriate concentration (e.g., 40 mg/kg/mouse/day). The mouse chow and immature corn leaves containing 6-MBOA or related compounds of the present invention was re-blended with some honey and water, and then dried. The mice in Groups 1 and 2 had food prepared the same way, without the addition of immature corn leaves containing 6-MBOA or related compounds of the present invention. All of the Groups were fed in the same manner on day 2 (Day −2) and day 1 (Day −1) prior to exposure to a stress procedure.

On day zero (Day 0), the mice in Groups 2 and 4 were stressed using a cold restraint stress procedure. As appreciated by those skilled in the art, the cold restraint stress procedure is a well described model that may result in a decreased immune response and greater susceptibility to infection. In the cold restraint stress procedure, the mice were placed in ventilated fifty (50) mL centrifuge tubes where they were able to move forward and backward, but were unable to turn around. The mice were then be placed in a refrigerator at 4° C. for about one (1) hour, then returned to their cages. The cold restraint stress procedure lacked tissue injury, and most closely resembled human psychologic stress and/or the shipping or other stresses that various animal species may experience (e.g., confinement, lack of food, lack of water, psychological distress, environmental changes, presence or absence of light, and the like) by analogy.

The immune measure chosen was the delayed hypersensitivity response to dinitrofluorobenzene (DNFB), an immunogenic agent. DNFB may sometimes be referred to as 1-fluor-2,4-dinitrobenzene, 2,4-dinitro-1-fluorobenzene, or Sanger reagent. The mice were exposed to DNFB via administration to ear skin on Days +1 and +2. In normal animals, the challenged areas may swell in response to the administration of DNFB, which may reflect a specific sensitization to this antigen. Such swelling typically represents inflammation and a measure of T-cell mediated immune response to DNFB. Animals which are stressed or injured or stressed in some way have blunted responses, reflecting immunosuppression. This response has also been associated with resistance to microbial infections.

On day 1 (Day +1) and day 2 (Day +2) following the stress procedure, all mice in Groups 1-4 were exposed to DNFB via administration to skin on the right ear pinna (i.e., ear skin). On Day +4, the thickness of the ear skin was measured with calipers on the exposed ear of each of the mice and the thickness of the ear skin on a contralateral ear (i.e., opposite ear non-exposed to DNFB). The ear skin thickness value of the non-exposed skin was subtracted from the ear skin thickness value of the DNFB exposed skin to quantify the level of immune response to DNFB.

The study protocol, presented hereinabove, may be summarized in Table 5, as follows:

| Day | Action |
| --- | --- |
| −3 | new mouse chow with/without 6-MBOA begun |
| −2 | new mouse chow with/without 6-MBOA continued |
| −1 | new mouse chow with/without 6-MBOA continued |
| 0 | Groups 2 and 4 exposed to cold stress procedure |
| +1 | All mice exposed to DNFB on right ear skin |
| +2 | All mice exposed to DNFB on right ear skin |
| +4 | All mice ears measured with calipers |

Statistical Analysis

The ear skin swelling results were analyzed using analysis of variance (ANOVA) and Fisher's Protected Least Square Difference (PLSD) tests.

Results

Referring generally now to FIG. 1, the stressed mice exhibited a depressed immune response compared to the unstressed mice. Moreover, the stressed mice that were fed immature corn leaves containing 6-MBOA or related compounds of the present invention showed normal levels of immune responsiveness to an immunogenic agent. More specifically, the cellular immune response to DNFB was determined by sensitizing the mice by topical application of DNFB. As illustrated in FIG. 1, the ordinate (vertical) axis represents the difference in thickness (i.e., swelling), measured in millimeters (mm), between the right ear pinna and the contralateral ear pinna. The abscissa (horizontal) axis represents a bar corresponding to each of the four mice Groups identified in this study.

In one presently preferred embodiment of the present invention, a solution of 0.25% DNFB (Sigma) was prepared in a 4:1 concentration of acetone-mineral oil mixture, and 10 microliters (µL) was applied to the back of the right ear pinna on Day +1 and Day +2. On Day +4, the ears were measured with a caliper to $10^{-3}$ mm. Swelling of the ear (higher measurement number) indicates an immune response to the DNFB, whereas the greater the swelling, the greater magnitude of response.

The results of the study showed a decrease in immune response in control stressed mice, as compared with all other Groups. Stressed mice exposed to immature corn leaves containing 6-MBOA or related compounds of the present invention had normal responses to the DNFB, suggesting that immature corn leaves containing 6-MBOA or related compounds of the present invention preserved cellular immune response in restraint stressed mice.

Example 9

Novel Compounds of the Invention in Preserving and/or Augmenting Innate Immune Defenses in Mice—Dosage Range Study Study Design Another study may be performed to evaluate the effect on cell mediated immune response from immature corn leaves containing 6-MBOA or related compounds of the present invention administered to stressed mice at a plurality of concentrations. The study protocol was similar to the one exercised in Example 8, with mice exposed to immature corn leaves containing 6-MBOA or related compounds of the present invention at dosage ranges of 40 mg/kg, 25 mg/kg and 5 mg/kg 6-MBOA (6-MBOA Dose #1, 2 and 3, respectively). The thickness of DNFB challenged ears was measured on day +4.

Male albino inbred strain mice, Balb/c (Charles River, Inc.), at about eight (8) weeks of age were used in this example. Balb/c mice may often be used in stress/injury animals because they may be more susceptible to stress and injury compared to other strains of animals. Those skilled in the art will appreciate that immune system changes are more easily observed in these animals.

It is anticipated that the mice that are stressed, but also exposed to immature corn leaves containing 6-MBOA or related compounds of the present invention (i.e., stressed/6-MBOA mice) may have the ability to mount an immune response to a known immunogenic agent. In contrast, those mice that may be stressed, but not exposed to immature corn leaves containing 6-MBOA or related compounds of the present invention (i.e., stressed/non-6-MBOA mice) may have little or no ability to mount an immune response to a known immunogenic agent. Likewise, additional control groups may utilize mice that are not stressed, and are not exposed to immature corn leaves containing 6-MBOA or related compounds of the present invention (i.e., non-stressed/non-6-MBOA mice) and mice that are stressed, but are not exposed to immature corn leaves containing 6-MBOA or related compounds of the present invention (i.e., stressed/non-6-MBOA mice).

Thirty-five (35) Balb/c mice were divided into six (6) groups. These groups comprised the following characteristics: Group 1 included a control group of non-stressed/non-6-MBOA mice; Group 2 included a control group of stressed/non-6-MBOA mice; Group 3 included a group of non-stressed/6-MBOA mice; Group 4 included a group of stressed/6-MBOA Dose #1 mice; Group 5 included a group of stressed/6-MBOA Dose #2 mice and Group 6 included a group of stressed/6-MBOA Dose #3 mice.

Beginning on day 3 prior (Day −3) to exposure to a stress procedure, immature corn leaves containing 6-MBOA or related compounds of the present invention was administered to the mice in Groups 3-6 orally via feed. The mouse chow was chopped into small bits, followed by the addition of immature corn leaves containing 6-MBOA or related compounds of the present invention at an appropriate concentration of 6-MBOA (e.g., 40 mg/kg/mouse/day). The mouse chow and immature corn leaves containing 6-MBOA or related compounds of the present invention were re-blended with some honey and water, and then dried. The mice in Groups 1 and 2 had food prepared the same way, without adding immature corn leaves containing 6-MBOA or related compounds of the present invention. All Groups were fed in the same manner on day 2 (Day −2) and day 1 (Day −1) prior to exposure to a stress procedure.

On day zero (Day 0) the mice in Groups 2 and 4 were stressed using a cold restraint stress procedure. As appreciated by those skilled in the art, the cold restraint stress procedure is a well described model that typically results in a decreased immune response and greater susceptibility to infection. In the cold restraint stress procedure, the mice were placed in ventilated fifty (50) mL centrifuge tubes where they were able to move forward and backward, but were unable to turn around. The mice may then be placed in a refrigerator at a temperature of about 4° C. for one (1) hour, then returned to their cages. The cold restraint stress procedure lacked tissue injury, and most closely resembled human psychologic stress and/or the shipping or other stresses that various animal species may experience (e.g., confinement, lack of food, lack of water, psychological distress, environmental changes, presence or absence of light, and the like) by analogy.

The immune measure that was chosen was the delayed hypersensitivity response to dinitrofluorobenzene (DNFB). The mice were exposed to DNFB via administration to ear skin on Days +1 and +2. In normal animals, the challenged areas may swell in response to the administration of DNFB, which may reflect a specific sensitization to this antigen. Such swelling typically represents inflammation and a measure of T-cell mediated immune response to DNFB. Animals which are stressed or injured or stressed in some way have blunted responses, reflecting immunosuppression. This response has also been associated with resistance to microbial infections.

On day 1 (Day +1) and day 2 (Day +2) following the stress procedure, all mice in Groups 1-6 were exposed to DNFB via administration to skin on the right ear pinna (i.e., ear skin). On Day +4, the thickness of the ear skin was measured with calipers on the exposed ear of each of the mice and the thickness of the ear skin on a contralateral ear (i.e., opposite ear non-exposed to DNFB). The ear skin thickness value of the non-exposed skin was subtracted from the ear skin thickness value of the DNFB exposed skin to quantify the level of immune response to DNFB.

The study protocol, presented hereinabove, may be summarized in Table 6, as follows:

| Day | Action |
| --- | --- |
| −3 | new mouse chow with/without 6-MBOA begun |
| −2 | new mouse chow with/without 6-MBOA continued |
| −1 | new mouse chow with/without 6-MBOA continued |
| 0 | Groups 2 and 4-6 exposed to cold stress procedure |
| +1 | All mice exposed to DNFB on right ear skin |
| +2 | All mice exposed to DNFB on right ear skin |
| +4 | All mice ears measured with calipers |

Statistical Analysis

The ear skin swelling and footpad swelling results were analyzed using analysis of variance (ANOVA) and Fisher's Protected Least Square Difference (PLSD) tests.

Results

Figure 2:
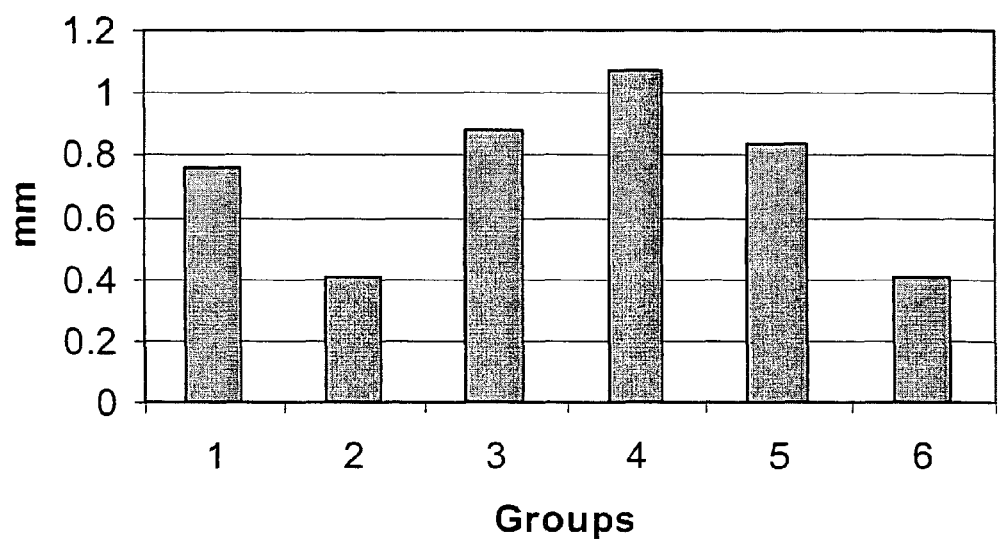
FIG. 2 is a bar chart illustrating an evaluation of the effects of one presently preferred embodiment of compounds of the present invention on preservation of cell-mediated immunity (CMI), manifested in response to dinitrofluorobenzene (DNFB) resulting from a study examining ear swelling in stressed and non-stressed mice exposed to one presently preferred embodiment of the compounds of the present invention (i.e., at concentrations of 40 mg/kg, 25 mg/kg, and 5 mg/kg) and the corresponding stressed and non-stressed control mice.

Referring now to FIG. 2, the stressed mice exhibited a depressed immune response compared to the unstressed mice. Moreover, stressed mice receiving immature corn leaves containing 6-MBOA or related compounds of the present invention at concentrations of 40 mg/kg and 25 mg/kg 6-MBOA had significantly greater immune responses than animals given immature corn leaves containing 6-MBOA or related compounds of the present invention at concentrations of 5 mg/kg 6-MBOA or no 6-MBOA.

Example 10

Novel Compounds of the Invention in Preserving and/or Augmenting Innate Immune Defenses in Calves Study Design A model for examining stress-induced changes in animals may involve subjecting animals to a stressful environment for a desired period of time sufficient to suppress innate immune responses, then subjecting the animals to an agent known to precipitate an immune response. Typically, the immune response may be measured by the amount of localized swelling (i.e., inflammation) that may occur near the administration site of the agent. The effects of a particular agent on the immune system of the animals may be examined by comparing the degree of swelling in control and experimental groups of the animals.

In the present study, immature corn leaves containing 6-MBOA or related compounds of the present invention were mixed with grain and fed to weaned calves who may be subjected to a stressful challenge (e.g., halter breaking). Evidence of biologic effects of supplementation with immature corn leaves containing 6-MBOA or related compounds of the present invention may be observed, suggesting that metabolism of 6-MBOA or related compounds of the present invention occurred and may indicate preservation and/or augmentation of immune response in stressed calves.

In one presently preferred embodiment of the present invention, the study facility included a barn with fencing, a squeeze chute, scale and an arena were the calves may be assembled for procedures. There was also a classroom utilized as a laboratory.

Thirty-two (32) calves were evenly divided into four (4) groups comprising eight (8) animals in each group. These four (4) groups comprised the following characteristics: Group 1 included a control group of non-stressed/non-6-MBOA calves; Group 2 included a group of stressed/non-6-MBOA calves; Group 3 included a group of stressed/6-MBOA Dose #1 calves and Group 4 included a group of stressed/6-MBOA Dose #2 calves.

The calves were mostly females (n=29), and also included a steer (n=1) and bulls (n=2). The calves were weaned for a period of at least two weeks. Stress was precipitated in the calves via roping. The calves had evidence of ring worm infection, but none of the calves exhibited an acute respiratory or other infection. The calves all appeared to have good appetites and readily consumed the grain rations.

The calves were housed outdoors in four separate corrals, with water and hay available ad libitum. The calves were fed sweet mix grain, with and without supplementation of immature corn leaves containing 6-MBOA or related compounds of the present invention. Beginning on day 1 prior (Day −1) to exposure to a stress procedure, the calves were fed once in the morning (8 am) on Day −1 and on Day 0 by spreading the grain ration over a shallow feed trough. Beginning on Day +1 and continuing until the end of the study, the calves were fed grain twice daily at 8 a.m. and 5 p.m. The calves lined up at the trough, and were observed to eat approximately equal amounts of the ration. Control groups (i.e., Groups 1 and 2)

and groups supplemented with immature corn leaves containing 6-MBOA or related compounds of the present invention (i.e., Groups 3 and 4) all received approximately ten (10) lbs of sweet mix grain twice daily. All rations were typically consumed within about five (5) minutes.

The stress procedure for this study involved halter breaking. Halter breaking included a 1.5 hour tie up (i.e., roping) at a fence in the arena. During this roping procedure, the calves were prevented from obtaining food or water. The roping occurred on Day 0 and was immediately followed with sensitizing of the calves necks with DNFB.

Immature corn leaves containing 6-MBOA or related compounds of the present invention may be weighed on a laboratory scale, and the appropriate amount for each group of 8 animals was added to seven (7) lbs of sweet mix grain and mixed thoroughly by hand. The sweet mix grain was somewhat sticky and the immature corn leaves containing 6-MBOA or related compounds of the present invention was well mixed. After the calves finished the supplemented ration, an additional three (3) lbs of grain was given to them.

Weight Measurements

Weights were obtained on the calves at Day −3, Day +4 and Day +11. Weights varied between calves, but there was no significant difference in starting weights between each of the Groups. There were no differences between Groups at any time point, whereas supplementation with immature corn leaves containing 6-MBOA or related compounds of the present invention did not inhibit weight gain of the calves.

Immune Response Assay

The cell mediated immune response was assessed in all calves using DNFB sensitization. The calves were placed in the chute on Day 0, a section of their left necks shaved and 100 ul 4% DNFB in acetone and mineral oil applied to the shaved area. On Day +1, this was repeated, using 400 ul DNFB on the same neck area. On Day +3, the calves right ear was shaved and 60 ul DNFB was applied to the shaved area. The sensitization area of the neck and normal neck skin was measured using a caliper. Twenty four (24) hours later, the challenged ear and the contra lateral ears were both measured, and the neck skin was re-measured and the data recorded. The data are expressed differences between normal and sensitized or challenged skin.

Immature corn leaves containing 6-MBOA or related compounds of the present invention was successfully mixed with grain and feed to the calves who readily consumed the rations.

Results

Figure 3:
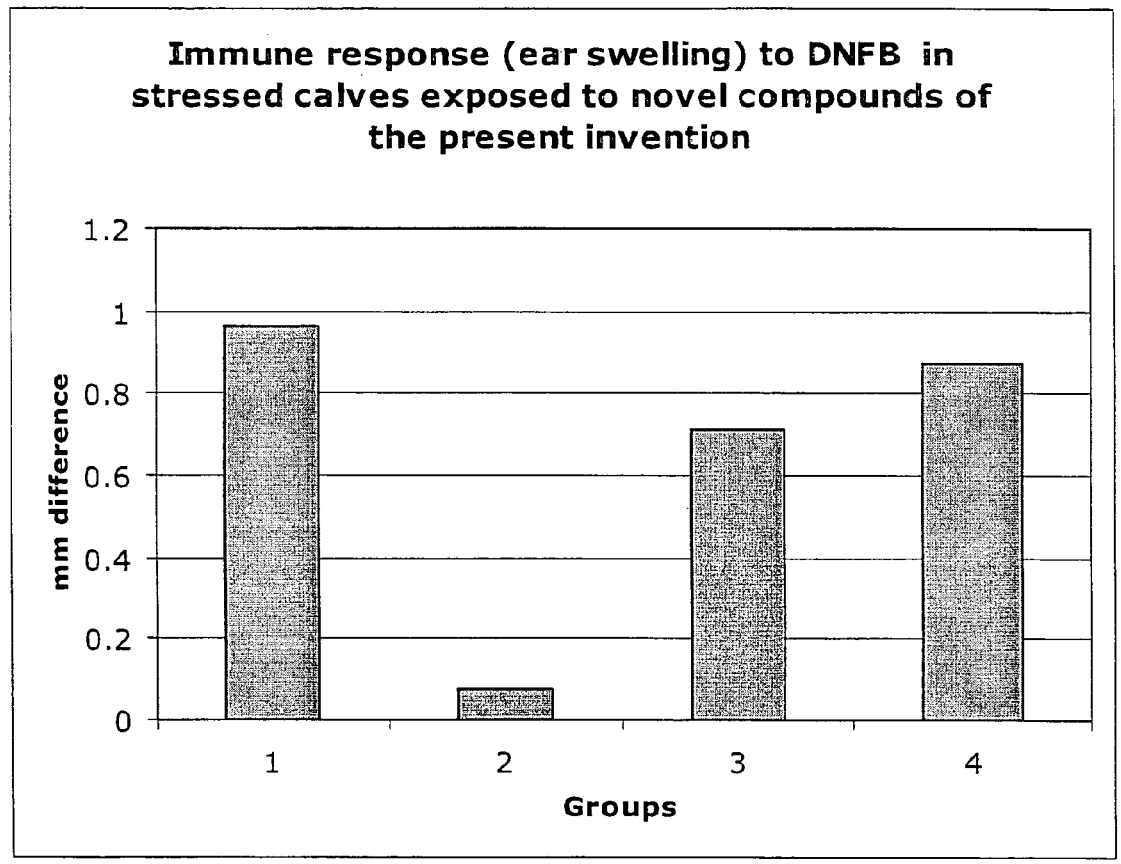
FIG. 3 is a bar chart illustrating one presently preferred embodiment of a method of the present invention showing a he cellular immune response to dinitrofluorobenzene (DNFB) resulting from a study examining ear swelling in stressed calves exposed to two (2) different dosages of one presently preferred embodiment of the compounds of the present invention and corresponding stressed and non-stressed control calves.

As observed in the mouse experiments referenced hereinabove, the immune response to a contact antigen was greater in calves exposed to immature corn leaves containing 6-MBOA or related compounds of the present invention as compared to stressed controls. Referring now to FIG. 3, immune response, measured both as degree of swelling at the sensitization site and at the challenged ear, was greater in the calves exposed to immature corn leaves containing 6-MBOA or related compounds of the present invention, as compared to the stressed controls. Immune response may be measured in millimeters difference using a caliper measuring device. As illustrated, Groups 3 and 4 were able to mount an immune response following exposure to DNFB.

Figure 4:
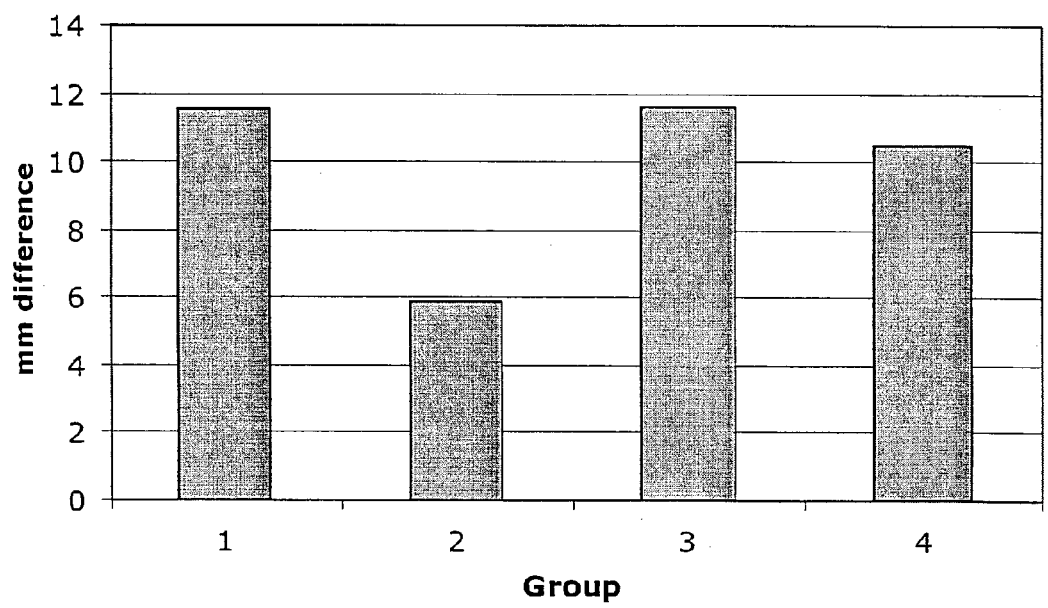
FIG. 4 is a bar chart illustrating one presently preferred embodiment of a method of the present invention showing the cellular immune response to dinitrofluorobenzene (DNFB) resulting from a study examining neck swelling in stressed calves exposed to two (2) different dosages of one presently preferred embodiment of the compounds of the present invention and corresponding stressed and non-stressed control calves.

Referring to FIG. 4, immune response, measured both as degree of swelling at the sensitization site and at the challenged area of the neck, was greater in the calves exposed to immature corn leaves containing 6-MBOA or related compounds of the present invention, as compared to the stressed controls. As illustrated, Groups 3 and 4 were able to mount an immune response following exposure to DNFB.

Discussion and Conclusions

In conclusion, it is apparent that supplementation with immature corn leaves containing 6-MBOA or related compounds of the present invention has positive effects in calves subjected to stress challenge. This was a robust observation, given the variability in the genetics and sizes of the calves, and the relatively poor condition of the subjects at the start of the experiment.

Example 11

Novel Compounds of the Invention in Preserving and/or Augmenting Innate Immune Defenses in Fish Fish farming, a form of aquaculture, has expanded at about eleven percent (11%) per year over the past decade. Fish farming may be the fastest growing sector of the world food economy. In 1990, thirteen (13) million metric tons of fish were produced. In comparison, thirty-one (31) million metric tons of fish were produced in 1998. To this end, fish farming has virtually overtaken cattle ranching as a primary food source worldwide. About eighty-five percent (85%) of fish farming occurs in developing countries. For example, China accounted for about twenty-one (21) million tons of the world aquacultural output in 1998, with India placing a distant second, at two (2) million tons.

Among industrial nations, the United States, Canada, Norway and Japan are the leaders in fish production. In North America and Europe, catfish, trout and salmon account for over eighty percent (80%) of finfish production. The current American annual output of 450,000 metric tons is primarily channel catfish (*Ictalurus punctatus*), while the 400,000 tons produced in Norway is primarily Atlantic salmon (*Salmo salar*). Farmed Atlantic salmon harvests in the United States have grown from 12,000 metric tons in 1990 to more than 50,000 metric tons in 2003.

Due to the crowded and stressed circumstances typical of fish farming, disease may be a frequent and a catastrophic limitation in successful fish farming. Hence, preferred embodiments of novel compounds of the present invention which may augment and/or enhance immune system function in fish and/or aquatic animals may have a significant impact in the quantitative and qualitative yield in the aquaculture industry. For example, a primary practice in finfish aquaculture, regardless of country, has been the prophylactic and episodic inclusion of antibiotics in feeds. Over thirty (30) metric tons of antibiotic active ingredient and about 6.5 to 14.3 metric tons of tetracycline were used in American fish feeds during 1999 alone. Pundits of this practice have suggested that major negative public health and ecological impacts may stem from this extensive use of antibiotic agents in the aquaculture industry.

These repercussions may include, for example and not by way of limitation, undesirable environmental consequences and human pathogens that may be resistant to particular antibiotics or classes of antibiotics. Indeed, escaped fish in the Broughton Archipelago, Queen Charlotte Strait, Canada, have been found with bacteria known to cause several human maladies, whereas the pathogens tested as being resistant to ten (10) different antibiotics.

About thirty percent (30%) of antibiotic-laden feed used in fish farms may actually be uneaten. This antibiotic-laden feed instead may move directly into the wild or natural food chain where it has been documented to kill natural marine algae, other plants and beneficial bacteria, as well as causing deformities in halibut larvae. Additional evidence that antibiotics go beyond the confines of fish farms may be shown in the seventy-five percent (75%) or more of wild fishes caught nearby with antibiotics in their flesh.

The increasing occurrence of antibiotic-resistant bacteria may also contribute to increased antibiotic use, and therefore greater environmental and human health risks associated with aquaculture. Preferably, antibiotic use in aquaculture may be minimized if the immune systems of cultured fish can be somehow enhanced to levels that improve disease resistance. Moreover, the European Union has begun to mandate lower permissible levels of antibiotics in fish feed due to concerns over environmental and human health consequences. As discussed, there may be a general ban on fish feed antibiotics in Europe which is anticipated to take effect on or about January, 2006. Likewise, governments of other countries may seriously consider similar legislation. The concerns of antibiotics in fish food may make immune system-stimulating feed additives highly desirous in the aquaculture industry. As contemplated herein, presently preferred embodiments of the compounds of the present invention may exist as preparations readily and widely recognized as safe for animal feed manufacture.

Fish may be a highly primitive form of vertebrates, but they have a typical vertebrate immune system that reacts and protects from pathogen attack. As in other vertebrates, the usual humoral and cellular responses characterize the immune system of fish. Indeed, the similarity of immune systems among vertebrates may be well evidenced by the extensive use of fish as experimental models for studying the vertebrate immune response. As appreciated by those skilled in the art, there may be a certain level equivalence of immune system physiology and function across vertebrate orders. Similar biochemical and physiological responses, whether in mammals and birds or in fish, may be logically anticipated through administration of preferred embodiments of the compounds of the present invention.

The term "generally regarded as safe" or GRAS may be a concept used worldwide to delineate items assessed as possible ingredients in feeds and may be considered to be safe for use in humans and the food chain. The GRAS concept simplifies the safety assessment process by eliminating GRAS ingredients from extensive and repetitive assessment. As appreciated, substances classified as GRAS include the leaves of monocotyledonous plants which, as disclosed herein, contain the compounds comprising the present invention.

Since the novel compositions of phenolic compounds and precursors of phenolic compounds of the present invention are configured to preserve and/or augment innate immune defenses, it will be readily appreciated that a method for preserving and/or augmenting innate immune defenses includes phenolic compounds belonging to related chemical families of which 6-MBOA is a member as described hereinabove and in the associated Figures. It is intended, therefore, that the examples provided herein be viewed as exemplary of the principles of the present invention, and not as restrictive to a particular structure or method for implementing those principles.

It will be further appreciated that the novel compositions of phenolic compounds and precursors of phenolic compounds belonging to related chemical families as defined herein and in the associated Figures of which 6-MBOA is a member, may be administered in any manner known to those ordinary skill in the art, including but not limited to, oral, parenteral, sublingual, topical, transdermal, intramuscular, or inhalation, and may also contain excipients chosen in accordance with the dosage form adopted. Moreover, the dosage of the extract compositions given to an individual may vary on the basis of several considerations without departing from the spirit and scope of the present invention and will, accordingly, depend on the targeted individual's particular case to be treated.

From the above discussion, the present invention provides novel compositions and methods of preserving and/or augmenting innate immune defenses in animals and humans using phenolic compounds and precursors of phenolic compounds belonging to related chemical families of which 6-MBOA is a member. It is contemplated by the inventors that presently preferred embodiments of the present invention for preserving and/or augmenting immune system defense may be administered to animals (e.g., fish, bird, reptile and mammal) and humans. Moreover, mammals may include bear (e.g., polar, grizzly, black, brown, panda and the like), buffalo, canine (e.g., wolf, fox, dog, coyote and the like), cow, deer (e.g., deer, moose, elk, antelope, caribou and the like), elephant, feline (e.g., cat, lion, tiger, cheetah, cougar, leopard, jaguar, lynx and the like), giraffe, goat, hippopotamus, horse, kangaroo, koala, manatee, primate (e.g., monkey, gorilla, chimpanzee, gibbon, baboon, orangutan, lemur, tamarin and the like), rhinoceros, rodent (e.g., mouse, rat, mole and the like), seal, sheep, sow, walrus, weasel (e.g., otter, beaver, badger, mink and the like), whale, yak and zebra.

While specific dose levels were used in the Examples and based upon absolute dosage ranges (e.g., 5 mcg to 60 mg) or dosage ranges individualized to body weight (e.g., 5 mg/kg to 40 mg/kg), the dosages are merely exemplary of some of the presently preferred embodiments of the present invention and are not intended to be restrictive thereof. Whereas, effective dose levels may vary to a large extent, and preferred dose levels may vary with the conditions being treated and the size or sex of the person being treated. To this end, dose levels do not appear to be critical as long as an effective amount is given.

Unlike prior art techniques or methods, the present invention provides novel chemical compositions derived, isolated and/or extracted from monocotyledonous plants or by chemical synthesis, and methods for using said compositions to: (1) preserve and augment innate immune defenses in humans and animals; (2) elevate levels of indoleamine, for example, serotonin and melatonin in humans and animals; (3) function as serotonin and/or melatonin analogs and/or agonists in mammals; (4) suppress the immunoregulatory effects of the hypothalamic-pituitary-adrenal (HPA) axis; (5) counteract the immunosuppressive effects of glucocorticoid hormones (e.g., cortisol); (6) counteract the immunosuppressive effects of catecholamine compounds (e.g., epinephrine and norepinephrine); (7) enhance T-cell proliferation and macrophage antigen presentation and (8) decrease complications associated with immune system abnormality (e.g., increased risk of infection and autoimmune reactions).

Example 12

Anxiety Behavior in Calves Placed in Stressful Situations

Compounds of the present invention which were obtained from the leaves of a monocotyledonous plant were successfully mixed with grain and fed to calves with a weight range of 160-300 lbs. The animals were fed between 20 mg/kg and 70 mg/kg of compounds of the present invention (e.g., ground corn leaves) daily and the calves, readily consumed the rations. There was no difference in weight gain between control and supplement fed calves over a one month period.

All of the calves showed anxiety behaviors in the squeeze chute (i.e., reluctance to enter the chute and pulling away from touch), but the additional challenge of receiving a halter for the first time, and being led/pulled into the arena and tied up appeared to be a significant stressor. It was observed that the supplement treated calves were calmer during the stress challenge.

The first two groups of calves that were handled were those calves that had been fed compounds of the present invention (e.g., ground corn leaves), followed by the control group of calves, which had not received corn leaves, just an equivalent amount of grain. There were differences in behavior during the chute manipulations between groups (controls were harder to get into the chute, and proceeded to buck and thrash more), and it was observed that following being tied up to the fence, the supplemented calves did not thrash around nor pull against the lead after a few minutes. In contrast, the control group pulled back from the fence, threw themselves against the fence and on the ground, and continued this behavior for most of the stress time period. The calves whose grain was supplemented with compositions of the present invention settled down after a few minutes, and just stood there, watching the thrashing control group of calves. Moreover, the supplemented calves were easier to untie and lead out of the arena at the end of the stress period, while the control group of calves were difficult to approach and generally resisted being untied and moved.

Example 13

Anxiety Behavior of High Spirited Dressage Horse

A high performance dressage horse exhibiting significant startle and resultant aggressive behaviors was fed 40 mg/kg compounds of the present invention (e.g., ground corn leaves) mixed in grain daily and observed for behavioral changes. Within 3 days of supplementation, the horse was noticeably quieter and easier to handle, while maintaining energy and performance ability. The owner has maintained the horse on 20 mg/kg for a long period and reports continued calming effects.

Example 14

Anxiety Associated with Weaning Horses

A Montana horse rancher participated in a study wherein the rancher had a historically challenging experience with weaning horses, with most foals becoming ill just after weaning, often with severe consequences including two deaths in the 2002 weaning season. In the 2003 season, the mares and foals were fed the equivalent of 20-40 mg/kg compounds of the present invention (e.g., ground corn leaves) mixed in grain before and after weaning for several days. Observers noted there was less vocalization at the time of separation of the mares and foals, and no illness was detected in the foals following weaning.

Example 15

Novel Compounds of the Invention in Tests of Anxiety in Mice

Tests for examining anxiety in mice involve subjecting the animals to a forced confrontation with a novel environment and/or exposure to predator odor. The effects of anti-anxiety agents on the anxiety level and emotional reactivity of the animals may be examined by comparing behavioral responses in control and experimental groups of the animals.

Female albino inbred strain mice, Balb/c (Charles River, Inc.), at about twelve to fourteen (12-14) weeks of age were selected for use in the present exemplary study. As appreciated by those skilled in the art, Balb/c mice are often used in anxiety testing because they are known to be especially sensitive to anxious settings and behavioral responses may be easily observed in these animals.

It was anticipated that Balb/c mice that were subjected to an anxiety-inducing situation, after being fed a preparation of immature corn leaves containing 6-MBOA or related compounds of the present invention (i.e., 6-MBOA mice), would demonstrate diminished behavioral responses associated with anxiety. For instance, it was expected that they would exhibit less timidity, be bolder in exploring their environment, and demonstrate less fear of potential predators. In contrast, it was anticipated that Balb/c mice, not fed preparations immature corn leaves containing 6-MBOA or related compounds of the present invention (i.e., non-6-MBOA mice) would demonstrate, to a greater degree than the 6-MBOA mice, behavioral responses associated with anxiety.

Study Design

In the present study, fourteen (14) female Balb/c mice were divided into two groups of seven (7) each. These groups comprised the following characteristics: (1) Group 1 included a control group of non-6-MBOA mice and (2) Group 2 included a group of dosed 6-MBOA mice (e.g., fed the preparation of immature corn leaves containing 6-MBOA or related compounds of the present invention). The non-6-MBOA mice were not given or dosed with 6-MBOA. All were placed, three to five (3-5) per cage, under a light/dark cycle of 12/12 hours. Lights came on at 6 am and went off at 6 pm. Temperature was maintained between about 21° C. and about 23° C. (about 70° F. and about 73° F.). Commercial rodent food pellets and water were freely available to both Group I and Group II.

For each of the five days prior to exposure to the anxiety test procedure, a preparation of immature corn leaves containing 6-MBOA or related compounds of the present invention at an appropriate concentration (e.g., 40 mg/kg/mouse/day) was administered orally to the mice in Group 2 via feed. For each of the five days prior to exposure to the anxiety test procedure, the mice in Group 1 had food prepared the same way, without the addition of immature corn leaves containing 6-MBOA or related compounds of the present invention.

After the five days, anxiety testing was performed using an open field testing apparatus wherein the mice, normally housed in small defined cage environments, were suddenly introduced into a larger plastic box having lateral dimensions of between about 35 cm and about 76.2 cm and a vertical dimension of about 20 cm. Peripheral sections were marked on the box and measured about 18 cm each. Preferably, paper toweling, which covered the box floor, was replaced before introduction of each test animal to remove scent residues from the previous tests. The box was illuminated with a 100 W light bulb except in one corner, which was designated the "safe corner" and which was shaded by a paper towel. A predator scent was introduced into a portion of the box by placing fresh dog feces, from a three year old domestic dog, in the center of the third quadrant of the box.

Mice were tested in the early dark phase between about 7:00 p.m. and about 10:00) p.m. A test consisted of gently placing a mouse into the safe corner of the box. This began a test phase where certain behavior responses of the mouse were recorded over a five (5) minute time period. During the test phase, the mouse was allowed to move about the box at will.

The behavioral response measures used to assess the reaction of the mice to the novel environment and predator odor were the time (in seconds) for: (1) the mouse to attempt to explore open field, (2) the number of entries of the mouse into peripheral portion of the open field, (3) the number of entries into the central portion of the open field, (4) the number of approaches directly towards predator odor object, (5) the number of stretching and/or exploratory behaviors, (6) the number of exhibits of defensive tail postures, and (7) the number of "frozen" posturing sessions.

The study results, presented as mean±standard error of the mean, for n=7, except otherwise indicated, are presented in Table 7, as follows:

| Behavioral Response Measure | Group 1 Non-6-MBOA mice | Group 2 6-MBOA mice | Significance (paired t test & ANOVA) |
|---|---|---|---|
| Time to initial attempt to explore open field | 40.67 ± 8.93 n = 6 | 19.33 ± 9.00 n = 6 | p < 0.21; *NS |
| Number of entries into peripheral portions of open field: | | | |
| Entries into nearest peripheral section | 2.83 ± 0.26 | 3.2 ± 0.26 | p < 0.51; NS |
| Entries into second nearest peripheral section | 2.0 ± 0.22 | 2.83 ± 0.26 | p < 0.05; Significant |
| Entries into third nearest peripheral section | 0.83 ± 0.40 | 2.0 ± 0.49 | p < 0.61; NS |
| Entries into furthest peripheral section | 0.33 ± 0.28 | 1.17 ± 0.46 | p < 0.05; Significant |
| Number of entries into central region of open field | 1.17 ± 0.34 | 1.68 ± 0.28 | p < 0.21; NS |
| Number of approaches directly towards predator object | 0.67 ± 0.28 | 1.33 ± 0.28 | p < 0.01; Significant |
| Number of stretching/exploratory behaviors | 3.17 ± 0.70 | 8.67 ± 0.94 | p < 0.01; Significant |
| Number of defensive tail postures | 2.17 ± 0.63 | 1.17 ± 0.46 | p < 0.21; NS |
| Number of "frozen" posturing sessions | 95.83 ± 22.58 | 10.83 ± 9.16 | p < 0.01; Significant |

*Not significant

Statistical Analysis

The significance of behavioral response differences were analyzed using paired t-tests and analysis of variance (ANOVA) with p<0.05.

Results

Referring generally now to Table 7, as was expected, the 6-MBOA mice of Group 2 exhibited less timidity, were bolder in exploring the open field environment, and demonstrated less fear of the potential predator scent. The control mice of Group 1 (non-6 MBOA mice) demonstrated a much longer mean time, as noted in Table 7, to initiate an attempt to explore the open field. Though the relatively large variability renders the results not significantly different by the measure used here, the difference in calculated means is in the anticipated direction, suggesting that the 6-MBOA mice may experience less hesitation in exploring a new environment than the non-6 MBOA mice.

Table 7 also suggests that the 6-MBOA mice of Group 2 had a greater tendency to explore the peripheral regions of the new open field environment. Specifically, more mean entries were recorded for the 6-MBOA mice than the non-6 MBOA control mice into every peripheral quadrant. In the case of the second quadrant and the most distant quadrant, quadrant four, the differences in mean values were significant.

Table 7 further suggests a slightly larger tendency of the 6-MBOA mice of Group 2 to explore the central region of the open field than the non-6-MBOA mice of Group, though the difference in mean values was not statistically significant. Both groups seemed to prefer the periphery of the open field over the central region.

A significant difference is seen, as set forth in Table 7, in the larger mean tendency of the Group 2 mice (6-MBOA mice) to approach the predator scent object. This implies that the 6-MBOA mice were less fearful than the control mice of Group 1.

A significant difference is also seen in the larger mean number of stretching postures observed for the 6-MBOA mice in comparison with the non-6-MBOA mice. As appreciated by those skilled in the art, stretch postures are usually a preliminary to locomotion. This again indicates less fear of the novel environment in the 6-MBOA mice over the non-6-MBOA mice.

Greater values for the mean number of defensive postures illustrated by the non-6-MBOA of Group 1 versus the 6-MBOA mice of Group 2, though not statistically significant, may again indicate less fear and anxiety in the 6-MBOA mice.

Finally, the mean tendency of the non-6-MBOA control mice of Group 1 to initiate a frozen posture, which is interpreted as a defensive or fearful response to novel stimulation, was significantly greater than for the 6-MBOA mice of Group 2. The fewer frozen postures and greater tendency of the 6-MBOA mice to move about and explore new environments and objects is therefore related to less anxiety and fear.

Generally, the results of this exemplary study showed a decrease in behavioral responses associated with anxiety and fear in the mice fed the preparation of immature corn leaves containing 6-MBOA or related compounds of the present invention (6-MBOA mice), as compared the non-6-MBOA mice. The differences in the mean values for the all of the behavioral response measurements were consistent with initial expectations. In five of the ten response categories, the differences in mean values was statistically significant. Mice exposed to immature corn leaves containing 6-MBOA or related compounds of the present invention had fewer anxiety related behavioral responses to the novel environments and fear inducing objects, suggesting that immature corn leaves containing 6-MBOA or related compounds of the present invention act as anti-anxiety agents in Balb/c mice.

Example 16

Anxiety Associated with Transportation and Loud Noises

A large, 12 year old mixed breed dog was given compounds of the present invention (e.g., ground corn leaves) in his daily ration of food. Prior to receiving the compounds of the invention the dog showed marked anxiety in multiple situations, (i.e., running away when the vacuum was near, trembling and destructive behavior when transported or left in a car). After receiving compounds of the present invention (30-40 mg/kg) for a few days, the dog's reaction to stressors was reduced significantly, especially the agitation associated with being transported. In general, the dog was calmer while maintaining his normal energy level.

Example 17

Calming Effect on Young Male Dog

A young, pure-bred Labrador retriever male obsessively collected items throughout the home of his owners, destroying the item if the owners didn't timely intervene. Within a few days of receiving compounds of the present invention (e.g., corn leaves) in the dog's food (30-40 mg/kg), this behavior, along with frequent barking and tail chasing, ceased. The observational results showed the young dog as being calmer.

As will be appreciated, the present invention may be embodied in other specific forms without departing from its spirit or essential characteristics. The described embodiments and examples are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A process for producing one or more chemical compounds defined as:

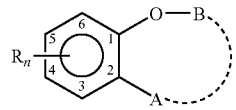

wherein "R" represents $C_1$-$C_4$ alkoxy, with the provision the R is in the 4 or 5 ring position;
wherein "n" represents one of the integers 0, 1 or 2;
wherein "B" represents H and "A" represents —OH, —$NH_2$ or NHCR', where R' denotes $C_1$-$C_4$ alkyl; and "B A" represents

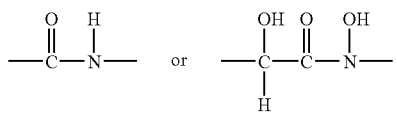

or pharmaceutically acceptable salts thereof, the process comprising the steps of:
  identifying at least one monocotyledonous plant that is a source of said one or more chemical compounds;
  growing said at least one monocotyledonous plant to an immature state;
  harvesting said at least one monocotyledonous plant while in the immature state;
  drying said at least one monocotyledonous plant at a temperature in a range of about 40° C. to about 45° C. to convert precursor compounds present in the monocotyledonous plant to one or more of the chemical compounds and produce a dried harvested plant containing phenols in total amounts greater than 17.0 mg/gm and combined amounts of 4-hydroxycinnamic acid and 4-hydroxy-3-methoxycinnamic acid totaling no more than 1.5 mg/gm (dry weight); and
  obtaining at least one chemical compound from said dried harvested plant.

2. A process as defined in claim 1, further producing by said process one or more chemical compounds defined as:

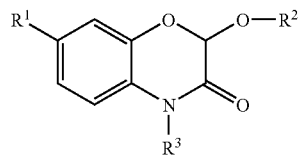

wherein "$R^1$" is selected from the group consisting of H and $OCH_3$;
wherein "$R^2$" is selected from the group consisting of H and Glucose (as a glucoside)
wherein "$R^3$" is selected from the group consisting of H, OH, and $OCH_3$; or
pharmaceutically acceptable salts thereof.

3. A process as defined in claim 1, wherein the source having one or more of the chemical compounds comprises a monocotyledonous plant selected from the group consisting of corn, wheat, barley, rye, oats, rice, sorghum, millet, bamboo, Job's Tears, barley-like grasses, and wild grasses.

4. A process as defined in claim 1, wherein said monocotyledonous plant is immature corn, *Zea mays*.

5. A process as defined in claim 4, wherein said immature corn has been grown to a height between about 45 centimeters and about 122 centimeters.

6. A process as defined in claim 4, wherein said immature corn has been grown to a height that does not exceed between about 30 centimeters and about 45 centimeters.

7. A process as defined in claim 4, wherein said immature corn has been grown for less than ten weeks after planting.

8. A process for producing one or more chemical compounds defined as:

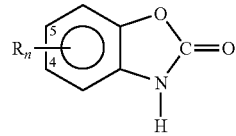

wherein "R" represents $C_1$-$C_4$ alkoxy, with stipulation that R is in the 4 or 5 ring position;
wherein "n" represents one of the integers 0, 1 or 2;
or pharmaceutically acceptable salts thereof, the process comprising the steps of:
  identifying at least one monocotyledonous plant that is a source of said one or more chemical compounds;
  growing said at least one monocotyledonous plant to an immature state;
  harvesting said at least one monocotyledonous plant while in the immature state;
  drying said at least one monocotyledonous plant at a temperature in a range of about 40° C. to about 45° C. to convert precursor compounds present in the monocotyledonous plant to one or more of the defined chemical compounds and produce a dried harvested plant containing phenols in total amounts greater than 17.0 mg/gm and combined amounts of 4-hydroxycinnamic acid and 4-hydroxy-3-methoxycinnamic acid totaling no more than 1.5 mg/gm (dry weight); and obtaining at least one of the chemical compounds from the dried harvested plant.

9. A process as defined in claim 8, wherein one of said chemical compounds comprise 6-methoxy-2,3-benzoxazolinone defined as:

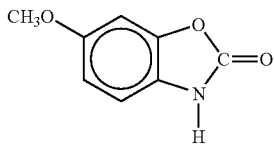

or one or more pharmaceutically acceptable salts thereof.

10. A process as defined in claim 8, wherein one of said chemical compounds comprise 5-methoxy-2,3-benzoxazolinone defined as:

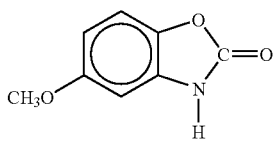

or one or more pharmaceutically acceptable salts thereof.

11. A process as defined in claim 8, wherein the source having one or more of the chemical compounds comprises a monocotyledonous plant selected from the group consisting of corn, wheat, barley, rye, oats, rice, sorghum, millet, bamboo, Job's Tears, barley-like grasses, and wild grasses.

12. A process as defined in claim 8, wherein said monocotyledonous plant is immature corn, *Zea mays*.

13. A process as defined in claim 12, wherein said immature corn has been grown to a height between about 45 centimeters and about 122 centimeters.

14. A process as defined in claim 12, wherein said immature corn has been grown to a height that does not exceed between about 30 centimeters and about 45 centimeters.

15. A process as defined in claim 12, wherein said immature corn has been grown for less than ten weeks after planting.

16. A process for producing one or more chemical compounds defined as:

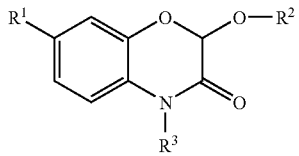

wherein "$R^1$" is selected from the group consisting of H and $OCH_3$;
wherein "$R^2$" is selected from the group consisting of H and Glucose (as a glucoside)
wherein "$R^3$" is selected from the group consisting of H, OH, and $OCH_3$; or pharmaceutically acceptable salts thereof, the process comprising the steps of:
identifying at least one monocotyledonous plant that is a source of said one or more chemical compounds;
growing said at least one monocotyledonous plant to an immature state;
harvesting said at least one monocotyledonous plant while in the immature state;
drying said at least one monocotyledonous plant in the immature state at a temperature in the range of between about 40° C. and about 45° C. so as to convert precursor compounds present in said at least one monocotyledonous plant to one or more of the chemical compounds and maximize conversion of precursors into active molecules; and
obtaining at least one of the chemical compounds from a dried harvested plant.

17. A process as defined in claim 16, wherein the source having one or more of the chemical compounds comprises a monocotyledonous plant selected from the group consisting of corn, wheat, barley, rye, oats, rice, sorghum, millet, bamboo, Job's Tears, barley-like grasses, and wild grasses.

18. A process as defined in claim 16, wherein said monocotyledonous plant is immature corn, *Zea mays*.

19. A process as defined in claim 18, wherein said immature corn has been grown to a height between about 45 centimeters and about 122 centimeters.

20. A process as defined in claim 18 wherein said immature corn has been grown to a height that does not exceed between about 30 centimeters and about 45 centimeters.

21. A process as defined in claim 18, wherein said immature corn has been grown for less than ten weeks after planting.

22. A process as defined in claim 16, wherein said dried harvested plant contains phenols in total amounts greater than 17.0 mg/gm (dry weight).

23. A process as defined in claim 16, wherein said dried harvested plant contains combined amounts of 4-hydroxycinnamic acid and 4-hydroxy-3-methoxycinnamic acid totaling no more than 1.5 mg/gm (dry weight).

24. A process for producing one or more chemical compounds defined as:

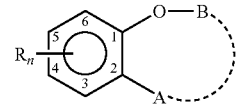

wherein "R" represents $C_1$-$C_4$ alkoxy, with the provision the R is in the 4 or 5 ring position;
wherein "n" represents one of the integers 0, 1 or 2;
wherein "B" represents H and "A" represents —OH, —$NH_2$ or NHCR', where R' denotes $C_1$-$C_4$ alkyl; and "B A" represents

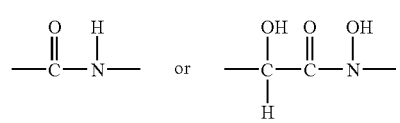

or pharmaceutically acceptable salts thereof, the process comprising the steps of:
identifying a monocotyledonous plant that is a source of one or more of the chemical compounds;

growing the monocotyledonous plant for a period less than ten weeks after planting and to a height between about 45 centimeters and about 122 centimeters;
harvesting the monocotyledonous plant;
drying the monocotyledonous plant at a temperature in the range of between about 40° C. and about 45° C. to convert precursor compounds present in said at least one monocotyledonous plant to one or more of the chemical compounds and maximize conversion of precursors to active molecules; and
obtaining at least one of the chemical compounds from a dried harvested plant.

* * * * *

UNITED STATES PATENT AND TRADEMARK OFFICE
CERTIFICATE OF CORRECTION

PATENT NO.        : 7,794,761 B2
APPLICATION NO.   : 11/178998
DATED             : September 14, 2010
INVENTOR(S)       : Shelby et al.

It is certified that error appears in the above-identified patent and that said Letters Patent is hereby corrected as shown below:

<u>Item 56, References Cited, OTHER PUBLICATIONS, Page 2</u>
Left Hand Column, change the reference "Leighton et al., "Substrate specificity of a glucosyltransferase and an N-hyroxylase involved in the biosynthesis of chyclic hydroxamic acids in Gramineae," *Phytochemistry*, 36(4): 887-892, 1994." to --Leighton et al., "Substrate specificity of a glucosyltransferase and an N-hydroxylase involved in the biosynthesis of cyclic hydroxamic acids in Gramineae," *Phytochemistry*, 36(4):887-892, 1994.--

Right Hand Column, change the reference "Urbanski et al., "Influence of photoperiod and 6-methoxybenzoxazolinone on the reproductive axis of inbred LSH/Ss Lak male hamester," *Journal of Reproduction and Fertility*, 90: 157-162, 1990." to --Urbanski et al., "Influence of photoperiod and 6-methoxybenzoxazolinone on the reproductive axis of inbred LSH/Ss Lak male hamsters," *Journal of Reproduction and Fertility*, 90: 157-162, 1990.--

Right Hand Column, change the reference "Sweat et al., "Uterotropic 6-methoxybenzoxazolinone is an adrenergic agonist and melatonin analog," *Molelcular Cellular Endocrinology*, 57: 131-138, 1988." to -- Sweat et al., "Uterotropic 6-methoxybenzoxazolinone is an adrenergic agonist and melatonin analog," *Molecular Cellular Endocrinology*, 57: 131-138, 1988.--

Right Hand Column, change the reference "Anderson et al., "Effects of melatonin and 6-methoxybenzoxazolinone on photoperiodic control of testis size in adult male golden hamseters," *Journal of Pineal Research*, 5: 351-65, 1988." to --Anderson et al., "Effects of melatonin and 6-methoxybenzoxazolinone on photoperiodic control of testis size in adult male golden hamsters," *Journal of Pineal Research*, 5: 351-65, 1988.--

<u>Column 4</u>
Line 40, after "claiming" remove [and]

<u>Column 7</u>
Line 40, before "cellular" remove [he]

<u>Column 8</u>
Lines 22-25, change all three instances of "Wherein" to --wherein--

Signed and Sealed this
Fifteenth Day of March, 2011

David J. Kappos
*Director of the United States Patent and Trademark Office*

Lines 38-40, change both instances of "Wherein" to --wherein--
Lines 53-55, change both instances of "Wherein" to --wherein--
Line 66, change "Wherein" to --wherein--

Column 9
Lines 1-2, change both instances of "Wherein" to --wherein--

Column 12
Line 44, change "pathway the," to --pathway, the--

Column 13
Line 62, change "a compounds" to --compounds--

Column 14
Line 67, after "effects" insert --and--

Column 15
Line 35, before "related" remove [are]

Column 18
Line 42, change "SEX" to --ASEX--
Line 48, change "SEX" to --ASEX--

Column 20
Line 18, after "HAD" insert --index--

Column 23
Line 9, change "1.20-.mu.g" to --1.20-µg--

Column 24
Line 66, change "Wherein" to --wherein--

Column 25
Lines 1-3, change both instances of "Wherein" to --wherein--
Line 17, after "now" insert --to--

Column 27
Line 2, after "shown" insert --as--
Line 6, after "with" insert --a--
Line 17, change "an glucoside" to --a glucoside--

Column 30
Line 56, change "then be placed" to --then placed--

Column 34
Line 38, change "were" to --where--

Column 35
Line 35, change "ul" to --µl--
Line 36, change "ul" to --µl--
Line 38, change "ul" to --µl--
Line 47, change "feed" to --fed--

Column 37
Line 65, change "those ordinary skill" to --those of ordinary skill--

Column 40
Line 21, before "immature corn leaves" insert --of--
Line 66, change "10:00)" to --10:00--

Column 41
Line 12, change "and/exploratory" to --and exploratory--

Column 42
Line 17, change "Group" to --Group 1--
Line 34, before "of Group 1" insert --mice--
Line 50, change "for the all" to --for all--

Column 44
Line 24, after "(as a glucoside)" insert --;--

Column 45
Line 65, after "(as a glucoside)" insert --;--